US007157248B2

(12) United States Patent  (10) Patent No.: US 7,157,248 B2
Qin et al.  (45) Date of Patent: Jan. 2, 2007

(54) CDNA ENCODING THE HUMAN α2 δ4 CALCIUM CHANNEL SUBUNIT

(75) Inventors: Ning Qin, Blue Bell, PA (US); Ellen Codd, Blue Bell, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 218 days.

(21) Appl. No.: 10/119,624

(22) Filed: Apr. 10, 2002

(65) Prior Publication Data

US 2003/0170785 A1 Sep. 11, 2003

Related U.S. Application Data

(63) Continuation-in-part of application No. 09/833,222, filed on Apr. 11, 2001.

(51) Int. Cl.
*C12N 15/00* (2006.01)
*C12N 15/12* (2006.01)
*C12N 15/63* (2006.01)
*C07K 14/00* (2006.01)
*C07H 21/04* (2006.01)

(52) U.S. Cl. ..................... 435/69.1; 435/6; 435/320.1; 435/325; 530/350; 536/23.1

(58) Field of Classification Search .................. 435/6, 435/69.1, 320.1, 325; 530/350; 536/23.1
See application file for complete search history.

(56) References Cited

U.S. PATENT DOCUMENTS 6,013,474 A   1/2000 Ellis et al.

FOREIGN PATENT DOCUMENTS

| WO | WO 96/39512 A | 12/1996 |
| WO | WO 00/20450 A2 | 4/2000 |
| WO | WO 01/08635 A | 2/2001 |
| WO | WO 01/19870 A2 | 3/2001 |

OTHER PUBLICATIONS

Klugbauer N et al. Molecular diversity of the calcium channel alpha2delta subunit. J Neurosci. Jan. 15, 1999;19(2):684–91.*
Yan et al., Two–amino acid molecular switch in an epithelial morphogen that regulates binding to two distinct receptors. Science 290: 523–527, 2000.*
Mickle JE et al. Genotype–phenotype relationships in cystic fibrosis. Med Clin North Am. May 2000;84(3):597–607.*
Voet et al. Biochemistry. 1990. John Wiley & Sons, Inc. pp. 126–128 and 228–234.*
Eck & Wilson in Goodman & Gilman's The Pharmacological Basis of Therapeutics, Ninth Edition, McGraw–Hill New York, 1996.*
U.S. Appl. No. 09/833,222, Qin et al.

Backonja, M. et al "Gabapetin for the Symptomatic Treatment of Painful Neuropathy in Patients With Diabetes Mellitus," JAMA. 1998, 280(21) 1831–1836.
Bean, B P, "Classes of Calcium Channels in Vertebrate Cells," Annual Rev. Physiol 1989. 51:367–84.
Bertolino. M, et al. "The Central Role of Voltage–Activated and Receptor–Operated Calcium Channels in Neuronal Cells," Annunal Rev. Pharmacol. Toxicol. Annu. 1992. 32:399–421.
Catterall. W A. "Structure and Regulation of Voltage–Gated Ca Channels," Annu Rev Cell Dev Biol 2000. 16:521–55.
Catterall. W.A., "Structure and Function of voltage–gated ion channels," Trends in Neurosciences. 1993. 16.500–506.
Catterall. W.A., "Structure and Function of Voltage–Sensitive Ion Channels," Science. 1988. 242:50–61.
Daniel. S., et al., "Screening for Potassium Channel Modulators by a High Through–Put 86 Rubidium Efflux Assay in a 96–Well Microtiter Plate," Journal of Pharmacol Methods. 1991. 25:185–193.
Dejongh. K. S. et al., "Subunits of Purified Calcium Channels," Journal of Biological Chemistry. 1990. 265(25) 14738–14741.
Ellis, S. B., et al., "Sequence and Expression of mRNAs Encoding the $α_2$ Subunits of a DHP–sensitive Calcium Channel," Science, 1988, 241:1661–1664.
Erfurth, A., et al., "An open label study of gabapentin in the treatment of acute mania," Journal of Psychiatric Research 1998 32:261–264.
Ertel, E. A., et al., "Nomenclature of Voltage–Gated Calcium Channels," Neuron. 2000. 25 533–535.
Evidente, V.G., et al., "Effective Treatment of Orthostatic Tremor With Gabapentin," Movement Disorders, 1998. 13(5)829–831.
Gee. N. S., et al., The Novel Anticonvulsant Drug, Gagapentin (Neurontin). Binds to the $α_2Ō$ Subunit of a Calcium Channel, Journal of Biological Chemistry, 1996, 271(10):5768–5776.
Gaild, B., et al., "Identification of the alternative spliced form of the α2/Ō subunit of voltage sensitive $Ca^2$ channels expressed in PC12 cells," Neuroscience Letters, 1995, 193:157–160.
Greenburg, D. A., "Calcium Channels in Neurological Disease," Annuals of Neurology, 1997, 42:275–282.

(Continued)

*Primary Examiner*—Joseph Murphy
(74) *Attorney, Agent, or Firm*—Myra McCormack

(57) ABSTRACT

The present invention provides nucleic acid and polypeptide sequences describing a novel isoform of the α2δ subunit of a voltage gated calcium channel, herein named as α2δ-4. The isolated nucleic acid or polypeptide molecule of the invention can be used in diagnosing and treating a disease or disorder associated with a defective α2δ-4 subunit, such as seizure-related syndromes, anxiety, multiple sclerosis, and the like.

6 Claims, 2 Drawing Sheets

OTHER PUBLICATIONS

Gurnett, C.A., et al., "Dual Function of the Voltage–Dependent $Ca^2$ Channel $\alpha_2\bar{o}$ Subunit in Current Stimulation and Subunit Interaction," Neuron. 1996. 16:431–440.

Holevinsky, K.O., et al., "ATP–sensitive K Channel Opener Acts as a Potent Cl Channel Inhibitor in Vascular Smooth Muscle Cells," J. Membrane Biol. 1994, 137:59–70.

Horowitz, B., et al., "Synthesis and Assembly of Functional Mammalian Na,K–ATPase in Yeast," Journal of Biological Chemistry, 1990, 265(8)4189–4192.

Hosey, M.M., et al., "L–Type Calcium Channels in Cardiac and Skeletal Muscle," Ann NY Acad Sci, 1990, 560:27–38.

Jacobson, M.A., et al., "Expression and secretion of biologically active echistatin Saccharomyces cerevisiae," Gene 1989, 85:511–516.

Jay, S.D., et al., "Primary Structure of the γ Subunit of the DHP–Sensitive Calcium Channel from Skeletal Muscle," Science, 1990, 248:490–92.

Jay, S.D., et al., "Structural Characterization of the Dihydropyridine–sensitive Calcium Channel $\alpha_2$–Subunit and the Associated $\bar{o}$ Peptides," Journal of Biological Chemistry: 1991, 266(5)3287–3293.

Kaufman, R.J., et al., Amplification and Expression of Sequences Contransfected with a Modular Dihydrofolate Reductase Complementary DNA Gene, 1982, J. Mol. Biol. 159:601–621.

Kok, K., et al., "Deletions of the Short Arm of Chromosome 3 in Solid Tumors and the Search for suppressor Genes," Advances in Cancer Research, 1997, 71:27–92.

Mazzini, L., et al., "The natural history and the effects of gabapentin in amyotrophic lateral sclerosis," Journal of the Neurological Sciences, 1998, 160:S57–S63.

Metz, Luanne, "Multiple Sclerosis: Symptomatic Therapies," Seminars in Neurology, 1998 18(3) 389–395.

Olson, W.L., et al., "Gabapentin for Parkinsonism A Double–Blind, Placebo–controlled, Crossover Trial," American Journal of Medicine, 1997, 102(1)60–6).

Qin, N. et al., "Modulation of human neuronal $\alpha_{1E}$–type calcium channel by $\alpha_2\bar{o}$–subunit," American J Physiol Cell Physiol, 1998 274 C1324–31.

Randall, A., et al., "Pharmacological Dissection of Multiple Types of $Co_{2x}$ Channel Currents in Rat Cerebeliar Granuie Neurons," Journal of Neuroscience, 1995, 15 2995–3012.

Riehl–Bellion. N. et al., "Purification and Biochemical Characterization of Recombinant Hirudin Produced by Saccharomyces cerevisiae," Biochemistry, 1989, 28 2941–2949.

Rinas, U. et al., "Characterization of Recombinant Factor Xllla Produced in Saccharomyces cerevisiae," Biotechnology 1990, 8:543–546.

Rock, D. et al., "Gabapentin actions on ligand– and voltage–gated responses in cultured rodent neurons," Epilepsy Research, 1993, 16 89–98.

Rorsmanm, P., et al., "Ion Channels, Electrical Activity and Insulin Secretion" Diabetes Metabolisme, 1994, 20: 138–145.

Rowbotham, M. et al., "Gabapentin for the Treatment of Postherpetic Neuralgia," JAMA, 1998, 280(1): 1837–1942.

Ruth, P., et al., Primary Structure of the β Subunit of the DHP–Sensitive Calcium Channel from Skeletal Muscle, Science, 1989, 245: 1115–1118.

Sieckevitz, M., et al., "Activation of the HIV–1 LTR by T Cell Mitogens and the Trans–Activator Protein of HTLV–1," Science, 1987, 238:1575–1578.

Singh, L., et al., "The antiepileptic agent gabapentin (Neurontin) possesses anxiolytic–like and antinociceptive actions tht are reversed by D–Serine," Psychopharmacology, 1996, 127(1)1–9.

Tanabe, T., et al., "Primary structure of the receptor for calcium channel blockers from skeletal muscle," Nature, 1987, 328:313–318.

Terwindt, G. M., et al., "Migraine, ataxia and epilepsy: a challenging spectrum of genetically determined calcium channelopathies," Eur Journal of Human Genetics, 1998, 64(4)297–307.

Tokumaru, H., et al., "A Calcium Channel from the Presynaptic Nerve Terminal of the Narke japonica Electric Organ Contains a Non–N–Type $\alpha_2\bar{o}$ Subunit," Journal of Neurochemistry, 1995, 65:831–836.

Vestergard–Bogind, B. "Single–File Diffusion through the $Ca^2$ –Activated K Channel of Human Red Cells," 1988, 88:67–75.

Watson, W.P. et al., "The Novel Anticonvulsant Gabapentin, Protects Against Both Convulsant and Anxiogenic Aspects of the Ethanol Withdrawl Syndrome," Neuropharmacology, 1997, 36(10) 1369–1375.

Wigler, M., et al., "Transfer of Purified Herpes Virus Thymidine Kinase Gene to Cultured Mouse Cells," Cell, 1977, 11:223–232.

Wiser, O., et al., "The $\alpha 2/\bar{0}$ subunit of voltage sensitive $Ca^2$ channels is a single transmembrance extracellular protein which is involved in regulated secretion," FEBS, 1996, 379:15–20.

International Search Report dated Dec. 17, 2003 for corresponding Appl. No. PCT/US02/11297.

Database EMBL Homo Sapiens 12p 13.3 PAC PRC15–1096D14, Aug. 4, 1998, SP 002313810 retrieved from EBI Database Accession AC005342.

Database EMBL Homo Sapiens Chromosome 12 Clone R0P11–76116 Mar. 17, 2001, XP002313811 retrieved from EBI, Database accession No. AC090840.

Database EMBL Homo Sapiens 12 BAC RP11–21K20, Aug. 4, 1998, XP002313813 retrieved from EBI, Database accession No. AC005343.

Database EMBL EST 7h46d04.X1 Dec. 15, 2000 XP002313813 retrieved from EBI Database Accession No. BF590937.

EP Examination dated Aug. 22, 2005 for Appl. No. 02 728 726.7.

EP Search Report dated Feb. 1, 2005 for EP Appl. No. 02 728 726.7.

* cited by examiner

SEQUENCE LISTING

<160> NUMBER OF SEQ ID NOS: 10

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence:
      oligonucleotide from N-terminal sequence of EST clone AAO01473

<400> SEQUENCE: 1 cagggctgg gctgcactgt ggtggtg                                         27

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence:
      oligonucleotide from N-terminal sequence of EST clone AAO01473

<400> SEQUENCE: 2
ctctcgggac ctcttggaga tcagaat                                        27

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:
      AP-1 primer

<400> SEQUENCE: 3
ccatcctaat acgactcact atagggc                                        27

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:
      AP-2 primer

<400> SEQUENCE: 4
actcactata gggctcgagc ggc                                            23

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:
????? calcium channel subunit protein

<400> SEQUENCE: 5
caggctctga gcctgcgagc tgag                                          24

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence:
????? calcium channel subunit protein

<400> SEQUENCE: 6
atgtcgtggt cgtggttgat gaccat                                        26

<210> SEQ ID NO 7
<211> LENGTH: 17
<212> TYPE: PRT
<213> ORGANISM: Artificial Sequence
<220> FEATURE:
<223> OTHER INFORMATION: Description of Artificial Sequence: synthetic
peptide from ????? calcium channel subunit protein

<400> SEQUENCE: 7

Lys Val Ser Asp Arg Lys Phe Leu Thr Pro Glu Asp Glu Ala Ser Val
 1               5                  10                  15

Cys

<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence: synthetic
peptide from ????? calcium channel subunit protein

<400> SEQUENCE: 8

Arg Val Glu Ala Asp Arg Gly Trp Ala Gly Phe Ser Ser Pro Asn Pro
 1               5                  10                  15

Leu Cys

<210> SEQ ID NO 9
<211> LENGTH: 3486
<212> TYPE: DNA
<213> ORGANISM: Homo sapiens

<400> SEQUENCE: 9
caggtacatt cagcagagcc caagtctgcc actctccaac cagaggccct ggaagcttgg      60
ggtcaagctc agtcctgggc tcgtcagccc ggccccacaa ccctcagcag gagaacctgc     120
cgaggacatt cagcacacag cagtgcagcc gctgggtcct gagggttctc cgcgtctcct     180
gcccaggcca tggctgtagc tttagggaca aggaggaggg acagagtgaa gctatgggct     240
gacaccttcg gcggggacct gtataacact gtgaccaaat actcaggctc tctcttgctg     300
cagaagaagt acaaggatgt ggagtccagt ctgaagatcg aggaggtgga tggcttggag     360

-continued

| | |
|---|---|
| ctggtgagga agttctcaga ggacatggag aacatgctgc ggaggaaagt cgaggcggtc | 420 |
| cagaatctgg tggaagctgc cgaggaggcc gacctgaacc acgaattcaa tgaatccctg | 480 |
| gtgttcgact attacaactc ggtcctgatc aacgagaggg acgagaaggg caacttcgtg | 540 |
| gagctgggcg ccgagttcct cctggagtcc aatgctcact tcagcaacct gccggtgaac | 600 |
| acctccatca gcagcgtgca gctgccacc aacgtgtaca caaagaccc agatatttta | 660 |
| aatggagtct acatgtctga agccttgaat gctgtcttcg tggagaactt ccagagagac | 720 |
| ccaacgttga cctggcaata ttttggcagt gcaactggat tcttcaggat ctatccaggt | 780 |
| ataaaatgga cacctgatga gaatggagtc attacttttg actgccgaaa ccgcggctgg | 840 |
| tacattcaag ctgctacttc tcccaaggac atagtgattt tggtggacgt gagcggcagt | 900 |
| atgaaggggc tgaggatgac tattgccaag cacaccatca ccaccatctt ggacaccctg | 960 |
| ggggagaatg acttcgttaa tatcatagcg tacaatgact acgtccatta catcgagcct | 1020 |
| tgttttaaag ggatcctcgt ccaggcggac cgagacaatc gagagcattt caaactgctg | 1080 |
| gtggaggagt tgatggtcaa aggtgtgggg gtcgtggacc aagccctgag agaagccttc | 1140 |
| cagatcctga agcagttcca agaggccaag caaggaagcc tctgcaacca ggccatcatg | 1200 |
| ctcatcagcg acggcgccgt ggaggactac gagccggtgt ttgagaagta taactggcca | 1260 |
| gactgtaagt ccgagttttt cacttacctc attgggagag aagtgtcttt tgctgaccgc | 1320 |
| atgaagtgga ttgcatgcaa caacaaaggc tactacacgc agatctcaac gctggcggac | 1380 |
| acccaggaga acgtgatgga ataccctgcac gtgctcagcc gccccatggt catcaaccac | 1440 |
| gaccacgaca tcatctggac agaggcctac atggacagca agctcctcag ctcgcaggct | 1500 |
| cagagcctga cactgctcac cactgtggcc atgccagtct tcagcaagaa gaacgaaacg | 1560 |
| cgatcccatg gcattctcct gggtgtggtg ggctcagatg tggccctgag agagctgatg | 1620 |
| aagctggcgc cccggtacaa gcttggagtg cacggatacg cctttctgaa caccaacaat | 1680 |
| ggctacatcc tctcccatcc cgacctccgg cccctgtaca gagagggaa gaaactaaaa | 1740 |
| cccaaaccta actacaacag tgtggatctc tccgaagtgg agtgggaaga ccaggctgaa | 1800 |
| tctctgagaa cagccatgat caatagggaa acaggtactc tctcgatgga tgtgaaggtt | 1860 |
| ccgatggata agggaagcg agttcttttc ctgaccaatg actacttctt cacgacatc | 1920 |
| agcgacaccc ctttcagttt ggggcggtg ctgtcccggg gccacggaga atacatcctt | 1980 |
| ctggggaaca cgtctgtgga agaaggcctg catgacttgc ttcacccaga cctggccctg | 2040 |
| gccggtgact ggatctactg catcacagat attgacccag accaccggaa gctcagccag | 2100 |
| ctagaggcca tgatccgctt cctcaccagg aaggacccag acctggagtg tgacgaggag | 2160 |
| ctggtccggg aggtgctgtt tgacgcgtg gtgacagccc ccatggaagc ctactggaca | 2220 |
| gcgctggccc tcaacatgtc cgaggagtct gaacacgtgg tggacatggc cttcctgggc | 2280 |
| acccgggctg gcctcctgag aagcagcttg ttcgtgggct ccgagaaggt ctccgacagg | 2340 |
| aagttcctga cacctgagga cgaggccagc gtgttcaccc tggaccgctt ccgctgtgg | 2400 |
| taccgccagg cctcagagca tcctgctggc agcttcgtct tcaacctccg ctgggcagaa | 2460 |
| ggaccagaaa gtgcgggtga acccatggtg gtgacggcaa gcacagctgt ggcggtgacc | 2520 |
| gtggacaaga ggacagccat tgctgcagcc gcggcgtcc aaatgaagct ggaattcctc | 2580 |
| cagcgcaaat tctgggcgg aacgcggcag tgcagcactg tggatgggcc gtacacacag | 2640 |
| agctgcgagg acagtgatct ggactgcttc gtcatcgaca caacgggtt cattctgatc | 2700 |
| tccaagaggt cccgagagac gggaagattt ctgggggagg tggatggtgc tgtcctgacc | 2760 |

-continued

```
cagctgctca gcatgggggt gttcagccaa gtgactatgt atgactatca ggccatgtgc    2820
aaaccctcga gtcaccacca cagtgcagcc cagcccctgg tcagcccaat ttctgccttc    2880
ttgacggcga ccaggtggct gctgcaggag ctggtgctgt tcctgctgga gtggagtgtc    2940
tggggctcct ggtacgacag aggggccgag gccaaaagtg tcttccatca ctcccacaaa    3000
cacaagaagc aggacccgct gcagccctgc gacacggagt accccgtgtt cgtgtaccag    3060
ccggccatcc gggaggccaa cgggatcgtg gagtgcgggc cctgccagaa ggtatttgtg    3120
gtgcagcaga ttcccaacag taacctcctc ctcctggtga cagaccccac ctgtgactgc    3180
agcatcttcc caccagtgct gcaggaggcg acagaagtca aatataatgc ctctgtcaaa    3240
tgtgaccgga tgcgctccca gaagctccgc cggcgaccag actcctgcca cgccttccat    3300
ccagaggtgc gggttgaggc ggatcgaggg tgggctggat tttcatcccc aaaccctctg    3360
tgcctgggtc tgtgcccctg cagacaggag catataggga tgccaatgaa cacacctgtg    3420
cctgtgcttc tcggggaaa cattcgcgtt tatgccctgt gacactgtga tataataaga    3480
aacaga                                                              3486
```

<210> SEQ ID NO 10
<211> LENGTH: 1090
<212> TYPE: PRT
<213> ORGANISM: Homo sapiens

<400> SEQUENCE: 10

```
Met Ala Val Ala Leu Gly Thr Arg Arg Arg Asp Arg Val Lys Leu Trp
 1               5                  10                  15

Ala Asp Thr Phe Gly Gly Asp Leu Tyr Asn Thr Val Thr Lys Tyr Ser
            20                  25                  30

Gly Ser Leu Leu Leu Gln Lys Lys Tyr Lys Asp Val Glu Ser Ser Leu
        35                  40                  45

Lys Ile Glu Glu Val Asp Gly Leu Glu Leu Val Arg Lys Phe Ser Glu
    50                  55                  60

Asp Met Glu Asn Met Leu Arg Arg Lys Val Glu Ala Val Gln Asn Leu
65                  70                  75                  80

Val Glu Ala Ala Glu Glu Ala Asp Leu Asn His Glu Phe Asn Glu Ser
                85                  90                  95

Leu Val Phe Asp Tyr Tyr Asn Ser Val Leu Ile Asn Glu Arg Asp Glu
            100                 105                 110

Lys Gly Asn Phe Val Glu Leu Gly Ala Glu Phe Leu Leu Glu Ser Asn
        115                 120                 125

Ala His Phe Ser Asn Leu Pro Val Asn Thr Ser Ile Ser Ser Val Gln
    130                 135                 140

Leu Pro Thr Asn Val Tyr Asn Lys Asp Pro Asp Ile Leu Asn Gly Val
145                 150                 155                 160

Tyr Met Ser Glu Ala Leu Asn Ala Val Phe Val Glu Asn Phe Gln Arg
                165                 170                 175

Asp Pro Thr Leu Thr Trp Gln Tyr Phe Gly Ser Ala Thr Gly Phe Phe
            180                 185                 190

Arg Ile Tyr Pro Gly Ile Lys Trp Thr Pro Asp Glu Asn Gly Val Ile
        195                 200                 205

Thr Phe Asp Cys Arg Asn Arg Gly Trp Tyr Ile Gln Ala Ala Thr Ser
    210                 215                 220

Pro Lys Asp Ile Val Ile Leu Val Asp Val Ser Gly Ser Met Lys Gly
225                 230                 235                 240
```

-continued

```
Leu Arg Met Thr Ile Ala Lys His Thr Ile Thr Ile Leu Asp Thr
            245                 250                 255

Leu Gly Glu Asn Asp Phe Val Asn Ile Ile Ala Tyr Asn Asp Tyr Val
        260                 265                 270

His Tyr Ile Glu Pro Cys Phe Lys Gly Ile Leu Val Gln Ala Asp Arg
    275                 280                 285

Asp Asn Arg Glu His Phe Lys Leu Leu Val Glu Leu Met Val Lys
290                 295                 300

Gly Val Gly Val Val Asp Gln Ala Leu Arg Glu Ala Phe Gln Ile Leu
305                 310                 315                 320

Lys Gln Phe Gln Glu Ala Lys Gln Gly Ser Leu Cys Asn Gln Ala Ile
                325                 330                 335

Met Leu Ile Ser Asp Gly Ala Val Glu Asp Tyr Glu Pro Val Phe Glu
            340                 345                 350

Lys Tyr Asn Trp Pro Asp Cys Lys Val Arg Val Phe Thr Tyr Leu Ile
        355                 360                 365

Gly Arg Glu Val Ser Phe Ala Asp Arg Met Lys Trp Ile Ala Cys Asn
370                 375                 380

Asn Lys Gly Tyr Tyr Thr Gln Ile Ser Thr Leu Ala Asp Thr Gln Glu
385                 390                 395                 400

Asn Val Met Glu Tyr Leu His Val Leu Ser Arg Pro Met Val Ile Asn
                405                 410                 415

His Asp His Asp Ile Ile Trp Thr Glu Ala Tyr Met Asp Ser Lys Leu
            420                 425                 430

Leu Ser Ser Gln Ala Gln Ser Leu Thr Leu Leu Thr Thr Val Ala Met
        435                 440                 445

Pro Val Phe Ser Lys Lys Asn Glu Thr Arg Ser His Gly Ile Leu Leu
    450                 455                 460

Gly Val Val Gly Ser Asp Val Ala Leu Arg Glu Leu Met Lys Leu Ala
465                 470                 475                 480

Pro Arg Tyr Lys Leu Gly Val His Gly Tyr Ala Phe Leu Asn Thr Asn
                485                 490                 495

Asn Gly Tyr Ile Leu Ser His Pro Asp Leu Arg Pro Leu Tyr Arg Glu
            500                 505                 510

Gly Lys Lys Leu Lys Pro Lys Pro Asn Tyr Asn Ser Val Asp Leu Ser
        515                 520                 525

Glu Val Glu Trp Glu Asp Gln Ala Glu Ser Leu Arg Thr Ala Met Ile
    530                 535                 540

Asn Arg Glu Thr Gly Thr Leu Ser Met Asp Val Lys Val Pro Met Asp
545                 550                 555                 560

Lys Gly Lys Arg Val Leu Phe Leu Thr Asn Asp Tyr Phe Phe Thr Asp
                565                 570                 575

Ile Ser Asp Thr Pro Phe Ser Leu Gly Ala Val Leu Ser Arg Gly His
            580                 585                 590

Gly Glu Tyr Ile Leu Leu Gly Asn Thr Ser Val Glu Glu Gly Leu His
        595                 600                 605

Asp Leu Leu His Pro Asp Leu Ala Leu Ala Gly Asp Trp Ile Tyr Cys
    610                 615                 620

Ile Thr Asp Ile Asp Pro Asp His Arg Lys Leu Ser Gln Leu Glu Ala
625                 630                 635                 640

Met Ile Arg Phe Leu Thr Arg Lys Asp Pro Asp Leu Glu Cys Asp Glu
                645                 650                 655
```

```
Glu Leu Val Arg Glu Val Leu Phe Asp Ala Val Val Thr Ala Pro Met
            660                 665                 670

Glu Ala Tyr Trp Thr Ala Leu Ala Leu Asn Met Ser Glu Glu Ser Glu
        675                 680                 685

His Val Val Asp Met Ala Phe Leu Gly Thr Arg Ala Gly Leu Leu Arg
    690                 695                 700

Ser Ser Leu Phe Val Gly Ser Glu Lys Val Ser Asp Arg Lys Phe Leu
705                 710                 715                 720

Thr Pro Glu Asp Glu Ala Ser Val Phe Thr Leu Asp Arg Phe Pro Leu
                725                 730                 735

Trp Tyr Arg Gln Ala Ser Glu His Pro Ala Gly Ser Phe Val Phe Asn
            740                 745                 750

Leu Arg Trp Ala Glu Gly Pro Glu Ser Ala Gly Glu Pro Met Val Val
        755                 760                 765

Thr Ala Ser Thr Ala Val Ala Val Thr Val Asp Lys Arg Thr Ala Ile
    770                 775                 780

Ala Ala Ala Ala Gly Val Gln Met Lys Leu Glu Phe Leu Gln Arg Lys
785                 790                 795                 800

Phe Trp Ala Ala Thr Arg Gln Cys Ser Thr Val Asp Gly Pro Tyr Thr
                805                 810                 815

Gln Ser Cys Glu Asp Ser Asp Leu Asp Cys Phe Val Ile Asp Asn Asn
            820                 825                 830

Gly Phe Ile Leu Ile Ser Lys Arg Ser Arg Glu Thr Gly Arg Phe Leu
        835                 840                 845

Gly Glu Val Asp Gly Ala Val Leu Thr Gln Leu Leu Ser Met Gly Val
    850                 855                 860

Phe Ser Gln Val Thr Met Tyr Asp Tyr Gln Ala Met Cys Lys Pro Ser
865                 870                 875                 880

Ser His His His Ser Ala Ala Gln Pro Leu Val Ser Pro Ile Ser Ala
                885                 890                 895

Phe Leu Thr Ala Thr Arg Trp Leu Leu Gln Glu Leu Val Leu Phe Leu
            900                 905                 910

Leu Glu Trp Ser Val Trp Gly Ser Trp Tyr Asp Arg Gly Ala Glu Ala
        915                 920                 925

Lys Ser Val Phe His His Ser His Lys His Lys Lys Gln Asp Pro Leu
    930                 935                 940

Gln Pro Cys Asp Thr Glu Tyr Pro Val Phe Val Tyr Gln Pro Ala Ile
945                 950                 955                 960

Arg Glu Ala Asn Gly Ile Val Glu Cys Gly Pro Cys Gln Lys Val Phe
                965                 970                 975

Val Val Gln Gln Ile Pro Asn Ser Asn Leu Leu Leu Val Thr Asp
            980                 985                 990

Pro Thr Cys Asp Cys Ser Ile Phe Pro Pro Val Leu Gln Glu Ala Thr
        995                 1000                1005

Glu Val Lys Tyr Asn Ala Ser Val Lys Cys Asp Arg Met Arg Ser Gln
    1010                1015                1020

Lys Leu Arg Arg Arg Pro Asp Ser Cys His Ala Phe His Pro Glu Val
1025                1030                1035                1040

Arg Val Glu Ala Asp Arg Gly Trp Ala Gly Phe Ser Ser Pro Asn Pro
                1045                1050                1055
```

-continued

```
Leu Cys Leu Gly Leu Cys Pro Cys Arg Gln Glu His Ile Gly Met Pro
            1060                1065                1070

Met Asn Thr Pro Val Pro Val Leu Leu Gly Gly Asn Ile Arg Val Tyr
        1075                1080                1085

Ala Leu
   1090
```

CDNA ENCODING THE HUMAN α2 δ4 CALCIUM CHANNEL SUBUNIT

BACKGROUND OF THE INVENTION

This application is a continuation-in-part of U.S. patent application Ser. No. 09/833,222 filed Apr. 11, 2001 and entitled "cDNA Encoding the Human Alpha2 Delta4 Calcium Channel Subunit". The contents of which are hereby incorporated by reference in its entirety.

Voltage gated calcium channels (VGCC) mediate $Ca^{2+}$ entry into cells in response to membrane depolarization (Catterall, W. A.(1988) *Science* 242:50–61 and Bean B P. (1989) *Annu. Rev. Physiol.* 51:367–368). $Ca^{2+}$ entering the cell through voltage-gated $Ca^{2+}$ channels serves as the second messenger of electrical signaling, initiating intracellular events such as contraction, secretion, synaptic transmission, and gene expression. Therefore, the VGCCs are involved in a variety of physiological processes in vertebrates, such as muscle contraction, insulin release from the pancreas, and neurotransmitter release in the nervous system (see Greenberg (1997), *Annals of Neurology*, 42:275–82; Rorsman et al. (1994), *Diabete Metab.* 20:138–145; and Catterall (1993), *Trends in Neurosciences* 16:500–506).

Electrophysiological studies reveal different types of calcium channels designated L-type (for Long Lasting), T-type (for Transient), N-type (for neither L nor T, or for "Neuronal"), P-type (for Purkinje cell), Q-type and R-type (for resistant) see Hess, (1990), *Ann. NY Acad. Sci.* 560:27–38; Bertolino and Llinás, (1992) *Annu. Rev. Pharmacol. Toxicol.* 32:399–421; and Randall and Tsien, (1995) *J. Neurosci.* 15:2995–3012). Except for the T type calcium channel, which is low voltage activated (LVA), the L-, N-, P-, Q- and R-types are all high voltage activated (HVA), i.e. their activation thresholds are normally above –40 mV.

The HVA $Ca^{2+}$ channels that have been characterized biochemically are complexes of a pore-forming $α_1$ subunit; a transmembrane, disulfide-linked complex of $α_2$ and δ subunits; an intracellular β subunit; and in some cases a transmembrane γ subunit. To date, molecular cloning of calcium channels has revealed that there are ten α1 subunits, four $α_2$δ complexes, four β subunits, and two γ subunits (Catterall, (2000), *Annu. Rev. Cell Dev. Biol.* 16: 521–555, and references therein). Analyses of these sequences indicate that the primary sequences of the calcium channel cDNAs have homologies ranging from between 40%–70%.

The primary structures of the five $Ca^{2+}$ channel subunits were determined by combination of protein chemistry with cDNA cloning and sequencing. The $α_1$ subunit is a protein of about 2000 amino acid residues with an amino acid sequence and predicted transmembrane structure like the previously characterized, pore-forming α subunit of the $Na^+$ channels (Tanabe et al. (1987) *Nature* 328:313–18). The amino acid sequence is organized in four repeated domains (I to IV), each of which contains six transmembrane segments (S1 to S6) along with a membrane-associated loop between transmembrane segments S5 and S6. The intracellular β subunit has predicted α helices but no transmembrane segments (Ruth et al., (1989) *Science* 245:1115–18). The γ subunit is a glycoprotein with four transmembrane segments (Jay et al. (1990) *Science* 248:490–92). The cloned $α_2$ subunit has many glycosylation sites and several hydrophobic sequences (Ellis et al. (1988) *Science* 241:1661–64), but biosynthesis studies indicate that it is an extracellular, extrinsic membrane protein attached to the membrane through disulfide linkage to the δ subunit (Gurnett et al (1996) *Neuron* 16:431–40). The δ subunit is encoded by the 3' end of the coding sequence of the same gene as the $α_2$ subunit. The mature forms of the $α_2$ and δ subunits are produced by post-translational proteolytic processing and disulfide linkage (De Jongh et al (1990) *J. Biol. Chem.* 265:14738–41; and Jay et al (1991) *J. Biol. Chem.* 266:3287–93).

The $α_2$δ subunit regulates most of the properties of the calcium channels, including voltage dependent kinetics and ligand binding (Qin et al, (1998) *Am J. Physiol. (Cell Physiol.)*, 274: C1324–31). Altered $α_2$δ expression is implicated in various disorders or diseases, such as epilepsy and other seizure-related syndromes, migraine, ataxia and other vestibular defects (for review see Terwindt et. al. (1998), *Eur J Hum Genet* 6(4):297–307), chronic pain (Backonja (1998), *JAMA*, 280(21):1831–6), mood, sleep interference (Rowbotham (1998), *JAMA*, 280(21):1837–42), anxiety (Singh et al. (1996), *Psychopharmocology*, 127(I): 1–9), ALS (Mazzini L et. al. (1998), *J Neurol Sci* 160 Suppl LS57–63), multiple sclerosis (Metz, (1998), *Semin Neurol*, 18(3):389–95), mania (Erfurth et al. (1998), *J Psychiatr Res*, 32(5):261–4), tremor (Evidente, et al. (1998), *Mov Disord*, 13(5):829–31), parkinsonism (Olson et al. (1997), *Am J Med*, 102(I):60–6), substance abuse/addiction syndromes (Watson et al. (1997), *Neuropharmacology*, 36(10):1369–75), depression, and cancer and at least one $α_2$δ gene is located in a region of the genome which is thought to harbor an important tumor suppressor gene (Kok et al. (1997), *Adv Cancer Res*, 71:27–92). The defective $α_2$δ gene has also been associated with proliferative diseases other than cancer, such as inflammation.

Characterizing the effects of the calcium channel subunit on ligand binding demonstrated that the $α_2$δ subunit alters the binding of neurological and cardiovascular drugs to the ion channel pore-forming $α_1$ subunit. Recently, gabapentin, a novel anticonvulsant drug, was shown to bind with high affinity directly to the calcium channel $α_2$δ subunit (Gee, et al. (1996) *J. Biol. Chem.* 271:5768–76). Gabapentin may control neuronal excitability by modifying calcium channel activity or expression (Rock et al, (1993) *Epilepsy Res.* 16:89–98). More interestingly, antibodies directed against the $α_2$δ subunit block secretion from PC12 cells, suggesting that the $α_2$δ subunit may play a distinct role in neurotransmitter release (Gilad et al (1995) *Neurosci. Lett.* 193:157–60; Tokumaru, et al. (1995) *J. Neurochem.* 65:831–836 and Wiser, et al. (1996) *FEBS Lett.* 379:15–20). Further more, treatment with compounds that bind to $α_2$δ leads to changes in the signal transduction mechanism of certain proteins including altered levels of MEK (MAP kinase kinase), an enzyme that activates the MAP kinase (mitogen-activated protein kinase). Activation of MAP kinase appears to be essential for cell proliferation and constitutive activation of this kinase is sufficient to induce cellular transformation.

An understanding of the pharmacology of compounds that interact with calcium channels and the design of such compounds is limited by an understanding of the genes that code for them. The identification of calcium channel subunits enables recombinant production of sufficient quantities of highly purified channel subunits which can be used in screening assays to identify or determine the effect of various compounds on channel function, thereby providing a basis for the design of therapeutic agents which affect the calcium channel. In particular, the identification of new α2δ subunits could present further possibilities for differential and specific regulation of calcium channels.

SUMMARY OF THE INVENTION

The present invention relates to isolated nucleic acid molecules encoding a novel isoform of human calcium channel α2δ subunit, herein referred to as α2δ-4, the polypeptides encoded by the isolated nucleic acid sequences, and the use of the nucleic acid molecules and polypeptides thereof.

DETAILED DESCRIPTION OF THE PREFERRED EMBODIMENTS

Definitions

Figure 1:
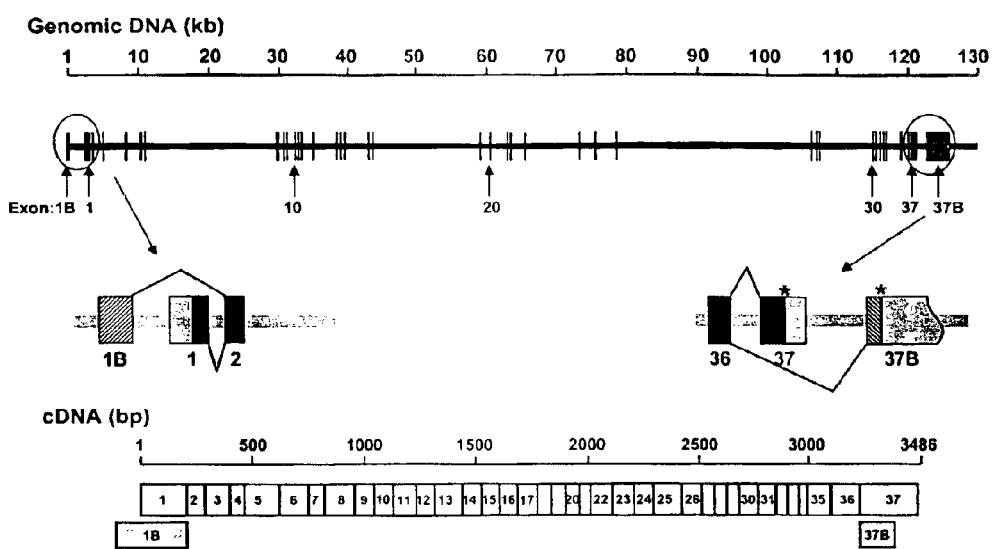
FIG. 1 illustrates the genomic structure of the human calcium channel α2δ-4 subunit.

The term "protein domain" as used herein refers to a region of a protein having a particular three-dimensional structure that has functional characteristics independent from the remainder of the protein. This structure may provide a particular activity to the protein. Exemplary activities include, without limitation, enzymatic activity, creation of a recognition motif for another molecule, or to provide necessary structural components for a protein to exist in a particular environment. Protein domains are usually evolutionarily conserved regions of proteins, both within a protein family and within protein superfamilies that perform similar functions.

The term "protein superfamily" as used herein refers to proteins whose evolutionary relationship may not be entirely established or may be distant by accepted phylogenetic standards yet show similar three dimensional structure or display a unique consensus of critical amino acids.

The term "protein family" as used herein refers to proteins whose evolutionary relationship has been established by accepted phylogenic standards.

The term "fusion protein" as used herein refers to protein constructs that are the result of combining multiple protein domains or linker regions. Fusion proteins can be created for the purpose of gaining the combined functions of the domains or linker regions. Fusion proteins can be created by molecular cloning of the nucleotide sequences to generate a contiguous nucleotide sequence encoding the fusion protein. Alternatively, creation of a fusion protein may be accomplished by chemically joining two proteins.

The term "linker region" or "linker domain" or similar such descriptive terms as used herein refers to one or more polynucleotide or polypeptide sequences that are used in the construction of a cloning vector or fusion protein. The function of a linker region can include introduction of cloning sites into the nucleotide sequence, introduction of a flexible component or space-creating region between two protein domains, or creation of an affinity tag to facilitate a specific molecular interaction. A linker region may be introduced into a fusion protein, if desired, during polypeptide or nucleotide sequence construction.

The term "cloning site" or "polycloning site" as used herein refers to a region of the nucleotide sequence that has one or more available restriction endonuclease consensus cleavage sequences. These nucleotide sequences may be used for a variety of purposes including, but not limited to, introduction of these sequences into DNA vectors to create novel fusion proteins, or to introduce specific site-directed mutations. It is well known by those of ordinary skill in the art that cloning sites can be engineered at a desired location by silent mutation, conserved mutation, or introduction of a linker region that contains desired restriction endonuclease recognition sequences. It is also well known by those of ordinary skill in the art that the precise location of a cloning site can be engineered into any location in a nucleotide sequence. The term "tag" as used herein refers to an amino acid sequence or a nucleotide sequence that encodes an amino acid sequence that facilitates isolation, purification or detection of a protein containing the tag. A wide variety of such tags are known to those skilled in the art and are suitable for use in the present invention. Suitable tags include, but are not limited to, HA peptide, polyhistidine peptides, biotin/avidin, and a variety of antibody epitope binding sites.

The terms "α2δ-4 gene", "nucleic acid encoding a α2δ-4 calcium channel subunit", and "α2δ-4 calcium channel subunit gene" as used herein, all refer to a DNA molecule comprising a nucleotide sequence that is substantially similar to that shown in SEQ ID NO: 9. The term "substantially similar" as used herein, includes identical sequences, as well as deletions, substitutions or additions to a polynucleotide or polypeptide sequence that maintain at least one biologically active portion thereof of the protein product and possess any of the conserved motifs. It is intended that as used herein, "α2δ-4 gene", "nucleic acid encoding a α2δ-4 calcium channel subunit", or "α2δ-4 calcium channel subunit gene", comprises a nucleotide sequence having at least a 70% identity to nucleotides 1 to 224 or 3308 to 3486 of SEQ ID NO:9, or comprises both a nucleotide sequence having at least a 70% identity to nucleotides 1 to 224 of SEQ ID NO:9 and a nucleotide sequence having at least a 70% identity to nucleotides 3308 to 3486 of SEQ ID NO:9. The terms "a α2δ-4 calcium channel subunit", "a calcium channel α2δ-4 subunit", and "a α2δ-4 protein" as used herein, all refer to a novel isoform of α2δ calcium channel subunit encoded by a α2δ-4 calcium channel subunit gene and further more include conservatively modified variants of the calcium channel subunit. The term "conservatively modified variant" as used herein is defined infra.

The term "a functional calcium channel" as used herein, refers to a calcium channel capable of mediating $Ca^{2+}$ influx in a cell. It is composed of at least a pore-forming α1 calcium channel subunit, an α2δ-4 calcium channel subunit and one or more additional calcium channel subunits, such as β and γ.

Unless defined otherwise, all technical and scientific terms used herein have the same meaning as is commonly understood by one of skill in the art.

Isolation of Human Calcium Channel α2δ-4 Subunit Nucleic Acid

Previously, three α2δ genes were identified and functionally characterized: α2δ-1 (Ellis et al., supra), α2δ-2 and α2δ-3 which is also named α2δ-C (WO00/20450). In addition, a fourth DNA molecule, α2δ-D, was cloned without functional characterization in WO00/20450. In the present invention, a novel α2δ gene termed herein as α2δ-4, was identified and functionally characterized. The complete sequence of the α2δ-4 gene as well as the encoded α2δ-4 calcium channel subunit was not known previously.

Cells naturally expressing the subunit can be used for α2δ-4 subunit cDNA isolation. Vertebrate cells naturally expressing the calcium channel α2δ-4 subunit include, but are not limited to, brain, heart and skeletal muscles. Other cells and cell lines may also be used to isolate calcium channel α2δ-4 subunit cDNA. The selection of other cells may be made after screening for calcium channel α2δ-4 subunit activity in cell extracts or in whole cell assays, described herein. Cells that possess calcium channel α2δ-4 subunit activity in these assays may be suitable for the isolation of calcium channel α2δ-4 subunit DNA or mRNA.

Any of a variety of procedures known in the art may be used to clone calcium channel α2δ-4 subunit DNA. One method is to direct functional expression of the calcium channel α2δ-4 subunit genes following the construction of a calcium channel α2δ-4 subunit-containing cDNA library in an appropriate expression vector system. Another method is to screen a calcium channel α2δ-4 subunit-containing cDNA library constructed in a bacteriophage or plasmid shuttle vector with a labeled oligonucleotide probe designed from all or part of the amino acid sequence of the calcium channel α2δ-4 subunit. An additional method includes screening a calcium channel α2δ-4 subunit-containing cDNA library constructed in a bacteriophage or plasmid shuttle vector with a partial cDNA encoding the calcium channel α2δ-4 subunit protein. This partial cDNA is obtained using specific PCR amplification of the calcium channel α2δ-4 subunit DNA fragments through the design of degenerate oligonucleotide primers from the amino acid sequence of the purified calcium channel α2δ-4 subunit protein.

Yet another method is to isolate RNA from calcium channel α2δ-4 subunit-producing cells and translate the RNA into protein via an in vitro or an in vivo translation system. The translation of the RNA into a peptide or a protein will result in the production of at least a portion of the calcium channel α2δ-4 subunit protein. This protein can then be identified by, for example, immunological reactivity with an anti-calcium channel α2δ-4 subunit antibody or by biological activity of calcium channel α2δ-4 subunit protein such as by measuring calcium influx or gabapentin binding to the α2δ-4 subunit. Alternatively, pools of RNA isolated from calcium channel α2δ-4 subunit-producing cells can be analyzed for the presence of an RNA that encodes at least a portion of the calcium channel α2δ-4 subunit protein. Further fractionation of the RNA pool can be performed to purify the calcium channel α2δ-4 subunit RNA from non-calcium channel α2δ-4 subunit RNA. The peptide or protein produced by this method may be analyzed to provide amino acid sequences, which in turn are used to provide primers for the production of calcium channel α2δ-4 subunit cDNA. The RNA that was used for translation can be analyzed to provide nucleotide sequences encoding a calcium channel α2δ-4 subunit and produce probes for the production of calcium channel α2δ-4 subunit cDNA. This method is known in the art and can be found in, for example, Maniatis, T., Fritsch, E. F., Sambrook, J. in Molecular Cloning: A Laboratory Manual, Second Edition, Cold Spring Harbor Laboratory Press, Cold Spring Harbor, N.Y. 1989.

It is readily apparent to those skilled in the art of molecular biology that other types of libraries, as well as libraries constructed from other cells or cell types, may be useful for isolating calcium channel α2δ-4 subunit-encoding DNA. Other types of libraries include, but are not limited to, cDNA libraries derived from other cells, libraries derived from a variety of organisms expressing other calcium channel α2δ-4 subunits, and from genomic DNA libraries that include YAC (yeast artificial chromosome) and cosmid libraries.

The selection of cells or cell lines for use in preparing a cDNA library to isolate calcium channel α2δ-4 subunit cDNA may be performed by first measuring cell associated calcium channel α2δ-4 subunit activity using the measurement of calcium channel α2δ-4 subunit-associated biological activity or using a ligand binding assay.

Preparation of cDNA libraries can be performed by standard techniques well known in the art. Well known cDNA library construction techniques can be found for example, in Maniatis, T., et al., supra. It is also readily apparent to those skilled in the art that DNA encoding a calcium channel α2δ-4 subunit may be isolated from a suitable genomic DNA library. Construction of genomic DNA libraries can be performed by standard techniques well known in the art. Well known genomic DNA library construction techniques are also found in Maniatis, T., et al., supra.

In order to clone the calcium channel α2δ-4 subunit gene by the above methods, knowledge of the amino acid sequence of calcium channel α2δ-4 subunit may be required. Calcium channel α2δ-4 subunit protein may be purified and partial amino acid sequences determined by automated sequenators. It is not necessary to determine the entire amino acid sequence, but the linear sequence of two regions of 6 to 8 amino acids from the protein can be determined for the production of primers for PCR amplification of a partial calcium channel α2δ-4 subunit DNA fragment.

Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the calcium channel α2δ-4 subunit sequence but will, under the appropriate hybridization conditions, be able to hybridize to calcium channel α2δ-4 subunit DNA. DNA isolated by these methods can be used to screen DNA libraries from a variety of cell types, from invertebrate and vertebrate sources, and to isolate homologous genes.

The purified biologically active calcium channel α2δ-4 subunit may have several different physical forms. The calcium channel α2δ-4 subunit may exist as a full-length nascent or unprocessed polypeptide, or as partially processed polypeptides or combinations of processed polypeptides. The full-length nascent calcium channel α2δ-4 subunit polypeptide may be post-translationally modified by specific proteolytic cleavage events resulting in the formation of fragments of the full length nascent polypeptide. A fragment or physical association of fragments may have the full biological activity associated with the calcium channel α2δ-4 subunit; however, the degree of calcium channel α2δ-4 subunit activity may vary between individual calcium channel α2δ-4 subunit fragments and physically associated calcium channel α2δ-4 subunit polypeptide fragments.

Because the genetic code is degenerate, more than one codon may be used to encode a particular amino acid. Therefore, the amino acid sequence can be encoded by any of a set of similar DNA oligonucleotides. Only one member of the set will be identical to the calcium channel α2δ-4 subunit sequence but will be capable of hybridizing to calcium channel α2δ-4 subunit DNA even in the presence of DNA oligonucleotides with mismatches under appropriate conditions. Under alternate conditions, the mismatched DNA oligonucleotides may still hybridize to the calcium channel α2δ-4 subunit DNA to permit identification and isolation of calcium channel α2δ-4 subunit encoding DNA.

DNA encoding a calcium channel α2δ-4 subunit from a particular organism may be used to isolate and purify homologues of calcium channel α2δ-4 subunits from other organisms. To accomplish this, the first calcium channel α2δ-4 subunit DNA can be used to hybridize with a sample containing DNA that encodes homologous calcium channel α2δ-4 subunits under appropriate hybridization conditions. The hybridized DNA complex may be isolated and the DNA encoding the homologous DNA can then be purified.

Polynucleotides and Polypeptides of the Present Invention

There is a substantial amount of redundancy in the various codons that code for specific amino acids. Therefore, this invention is also directed to those DNA sequences that contain alternative codons that code for the translation of the identical amino acid. For purposes of this specification, a nucleic acid sequence having one or more codons that vary yet still encode an identical amino acid sequence will be defined as a degenerate variation. Nucleic acid sequences with degenerate variations are contemplated within the scope of this invention.

Also included within the scope of this invention are sequences that include mutations either in the DNA sequence or the translated protein, which do not substantially alter the ultimate physical properties of the expressed protein. For example, substitution of aliphatic amino acids alanine, valine, leucine and isoleucine; interchange of the hydroxyl residues serine and threonine; exchange of the acidic residues aspartic acid and glutamic acid; substitution between the amide residues asparagine and glutamine; exchange of the basic residues lysine and arginine; and substitution among the aromatic residues phenylalanine and tyrosine may not cause a change in functionality of the polypeptide. Such substitutions, often termed conservative mutations resulting in "conservatively modified variants", where they have been manipulated in a laboratory setting or are naturally occurring, are well known and are described, for instance in Molecular Biology of the Gene, 4th Ed. Bengamin Cummings Pub. Co. by Watson et al.

It is known that DNA sequences coding for a peptide may be altered to code for peptides having properties that are different from those of the naturally occurring peptide. Methods of altering DNA sequences include, but are not limited to, site directed mutagenesis, chimeric substitution, and gene fusion. Site-directed mutagenesis is used to change one or more DNA residues that may result in a silent mutation, a conservative mutation, or a nonconservative mutation. Chimeric genes can be prepared by replacing domains within the calcium channel α2δ-4 subunit gene with domains from similar or different genes. Fusion genes may be prepared by adding domains or gene fragments from other genes to the calcium channel α2δ-4 subunit gene. Examples of fusion genes include genes encoding a protein containing an affinity tag to facilitate identification and isolation of the fusion gene or of the resulting protein. Fusion genes may be prepared by creating a soluble version of the protein by, for example, removing one or more transmembrane domains or by adding a targeting sequence to redirect the normal transport of the protein. Alternatively, fusion genes can be prepared that add new post-translational modification sequences to the calcium channel α2δ-4 subunit gene. Such mutations can be used to alter the binding properties of a protein. Examples of altered properties include, but are not limited to, changes in the affinity of an enzyme for a substrate or a receptor for a ligand. Such changes can be used to create useful variants of the present invention so long as the original function (i.e., the ability of the subunit gene to form a functional calcium channel) of the polynucleotide or polypeptide sequence of the present invention is maintained as described herein.

Identity or similarity, as known in the art, refers to the relationship between two or more polypeptide sequences or two or more polynucleotide sequences as determined by comparing the sequences. In the art, identity also refers to the degree of sequence relatedness between polypeptide or polynucleotide sequences, as the case may be, as determined based on the extent of matches between strings of such sequences. Both identity and similarity can be readily calculated (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). While there exists a number of methods to measure identity and similarity between two polynucleotide or two polypeptide sequences, both terms are well known to skilled artisans (Sequence Analysis in Molecular Biology, von Heinje, G., Academic Press, 1987; Sequence Analysis Primer, Gribskov, M. and Devereux, J., eds., M Stockton Press, New York, 1991; and Carillo, H., and Lipman, D., (1988) SIAM J. Applied Math., 48, 1073. Methods commonly employed to determine identity or similarity between sequences include, but are not limited to, those disclosed in Carillo, H., and Lipman, D., supra. Preferred methods to determine identity are designed to give the largest match between the sequences tested. Methods to determine identity and similarity are codified in computer programs. Preferred computer program methods to determine identity and similarity between two sequences include, but are not limited to, GCG program package (Devereux, J., et al., (1984) Nucleic Acids Research 12(1), 387), BLASTP, BLASTN, and FASTA (Atschul, S. F. et al., (1990) J. Molec. Biol. 215, 403).

The term "polynucleotide(s)" or "nuclei acid molecule(s)" as used herein refers to any polyribonucleotide or polydeoxribonucleotide which may be unmodified RNA or DNA or modified RNA or DNA. Thus polynucleotides, as used herein, refers to, among others, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded, or a mixture of single- and double-stranded regions. In addition, polynucleotide as used herein also refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide includes DNAs or RNAs as described above that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including both eukaryotic and prokaryotic cells. The term "polynucleotides" further is used herein to include short polynucleotides often referred to as oligonucleotide(s).

The term "polypeptides" or "protein(s)", as used herein, refers to the basic chemical structure of polypeptides that is well known and has been described in textbooks and other publications in the art. In this context, the term is used herein to refer to any peptide, polypeptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, but also by chemical modification techniques which are well known to the art. Even the common modifications that occur naturally in polypeptides are too numerous to list exhaustively here, but they are well described in basic texts and in more detailed monographs, as well as in a voluminous research literature and they are well known to those of skill in the art.

The polypeptides of the present invention may include known modifications such as acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill in this art and have been described in great detail in the scientific literature. Several particularly common modifications including, but not limited to, glycosylation, lipid attachment, sulfation, gamma-carboxylation of glutamic acid residues, hydroxylation and ADP-ribosylation are described in most basic texts, such as, for example Proteins—Structure and Molecular Properties, 2nd Ed., T. E. Creighton, W. H. Freeman and Company, New York (1993). Many detailed reviews are available on this subject, such as, for example, those provided by Wold, F., Post-translational Protein Modifications: Perspectives and Prospects, pgs. 1–12 in Post-translational Covalent Modification of Proteins, B. C. Johnson, Ed., Academic Press, New York (1983); Seifter et al., (1990) Meth. Enzymol. 182: 626–646 and Rattan et al., "Protein Synthesis: Posttranslational Modifications and Aging", (1992) Ann. N.Y. Acad. Sci. 663: 48–62.

It will be appreciated, as is well known and as noted above, that polypeptides are not always entirely linear. For instance, the term "polypeptide" further includes molecules that may not occur naturally, but may be the product of, for example, post-translational events or further human manipulation. Examples of these polypeptides include circular, branched and branched circular polypeptides that can be synthesized by non-translation natural processes and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For example, the amino terminal residue of polypeptides made in E. coli or other cells, prior to proteolytic processing will almost invariably be N-formylmethionine. During post-translational modification of the peptide, a methionine residue at the NH2-terminus may be deleted. Accordingly, this invention contemplates the use of both the methionine-containing and the methionineless amino terminal variants of the protein of the invention.

The modifications that occur in a polypeptide often will be a function of how it is made. For polypeptides made by expressing a cloned polynucleic acid sequence in a host, for instance, the nature and extent of the modifications in large part will be determined by the host cell posttranslational modification capacity and the modification signals present in the polypeptide amino acid sequence. For example, as is well known, glycosylation often does not occur in bacterial hosts such as, for example, E. coli. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation. Similar considerations apply to other modifications.

It will be appreciated that the same type of modification may be present in the same or varying degree at several sites in a given polypeptide. Also, a given polypeptide may contain many types of modifications. In general, as used herein, the term polypeptide encompasses all such modifications, particularly those that are present in polypeptides synthesized recombinantly by expressing a polynucleotide in a host cell.

The term "variant(s)" as used here in refers to polynucleotides or polypeptides that differ from a reference polynucleotide or polypeptide, respectively. A variant of a polynucleotide may be a naturally occurring variant such as a naturally occurring allelic variant or it may be a variant that is not known to occur naturally.

Polynucleotide variants are those that differ in nucleotide sequence from another reference polynucleotide. Generally, differences are limited so that the nucleotide sequences of the reference and the variant are closely similar overall and, in many regions, identical. As noted below, changes in the nucleotide sequence of the variant may be silent. That is, the change may not alter the amino acids encoded by the polynucleotide. Where alterations are limited to silent changes of this type a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed above.

A polypeptide variant refers to polypeptides that differ in amino acid sequence from another, reference polypeptide. Generally, differences are limited so that the sequences of the reference and the variant are closely similar overall and, in many regions, identical. A variant and reference polypeptide may differ in amino acid sequence by one or more substitutions, additions, deletions, fusions and truncations, which may be present in any combination. As used herein, a "functional derivative" of an α2δ-4 calcium channel subunit is a compound that possesses a biological activity (either functional or structural) that is substantially similar to the biological activity of the α2δ-4 calcium channel subunitprovided in SEQ ID NO:10. The term "functional derivatives" is intended to include the "fragments," "variants," "degenerate variants," "analogs" and "homologues" or to "chemical derivatives" of calcium channel α2δ-4 subunits. Useful chemical derivatives of polypeptides are well known in the art and include, for example covalent modification of one or more reactive organic sites contained within the polypeptide with a secondary chemical moiety. Well known cross-linking reagents are useful to react to amino, carboxyl, or aldehyde residues to introduce, for example an affinity tag such as biotin, a fluorescent dye, or to conjugate the polypeptide to a solid phase surface (for example to create an affinity resin).

The term "fragment" is meant to refer to any polypeptide subset of a calcium channel α2δ-4 subunit. A molecule is "substantially similar" to a calcium channel α2δ-4 subunit if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the entire calcium channel α2δ-4 subunit molecule or to a fragment thereof.

One embodiment of polynucleotides of the invention is a nucleic acid molecule comprising a nucleotide sequence having at least a 70% identity to nucleotides 1 to 224 of SEQ ID NO:9; or a complement thereof. Preferably, the polynucleotide of the invention is a nucleic acid molecule comprising at least 15 sequential bases of nucleotides 1 to 224 of SEQ ID NO:9, or a complement thereof. More preferably, the polynucleotide of the invention encoding a α2δ calcium channel subunit protein comprising a nucleotide sequence having at least a 85% identity to nucleotides 1 to 224 of SEQ ID NO:9, or a complement thereof.

Another embodiment of the polynucleotides of the invention is a nucleic acid molecule comprising a nucleotide sequence having at least a 70% identity to nucleotides 3308 to 3486 of SEQ ID NO:9; or a complement thereof. Preferably, the polynucleotide of the invention is a nucleic acid molecule comprising at least 15 sequential bases of nucleotides 3308 to 3486 of SEQ ID NO:9, or a complement thereof. More preferably, the polynucleotide of the invention is a polynucleotide encoding an α2δ calcium channel subunit protein comprising a nucleotide sequence having at least a 85% identity to nucleotides 3308 to 3486 of SEQ ID NO:9, or a complement thereof.

Yet another embodiment of the polynucleotides of the invention is a nucleic acid molecule comprising both a nucleotide sequence having at least a 70% identity to nucleotides 1 to 225 and a nucleotide sequence having at least a 70% identity to nucleotides 3308 to 3486 of SEQ ID NO:9; or a complement thereof. Preferably, the polynucleotide of the invention encoding a α2δ calcium channel subunit protein comprising both a nucleotide sequence having at least a 85% identity to nucleotides 1 to 225 and a nucleotide sequence having at least a 85% identity to nucleotides 3308 to 3486 of SEQ ID NO:9; or a complement thereof Particularly preferred polynucleotides of this invention encode variants, analogs, derivatives and fragments of SEQ. ID. NO.:9, and variants, analogs and derivatives of the fragments, which have the amino acid sequence of the polypeptide of SEQ. ID. NO.:10 in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the protein encoded by the nucleic acid of SEQ. ID. NO.:9. Also especially preferred in this regard are conservative substitutions. Most highly preferred are polynucleotides encoding polypeptides having the amino acid sequence of SEQ. ID. NO.:10, without substitutions.

Preferred embodiments of the invention are polynucleotides that are at least 94% identical over their entire length to the polynucleotide sequence set out in SEQ. ID. NO:9, and polynucleotides which are complementary to such polynucleotides.

Another preferred embodiment of the invention are polynucleotides that encode polypeptides which are at least 96% identical over their entire length to amino acid sequences set out in SEQ ID NO:10, and polynucleotides which are complementary to such polynucleotides.

The present invention further relates to polynucleotides that hybridize to the herein above-described sequences. In this regard, the present invention especially relates to polynucleotides that hybridize under stringent conditions to the herein above-described polynucleotides. There are a large numbers of polynucleotide hybridization techniques known in the art including hybridizations coupling DNA to DNA, RNA to RNA and RNA to DNA. All of these methods can incorporate stringent hybridization conditions to facilitate the accurate identification of nucleic acid targeting to a hybridizable probe. As is known in the art, methods vary depending on the substrate used for hybridization and Maniatis et al. supra, as well as a variety of references in the art detail a number of stringent hybridization techniques. As used herein, the term "stringent hybridization conditions" refers to hybridization of a nucleic acid molecule on a filter support to a probe of interest at 42° C. for about 8 to 24 hours in a low salt hybridization buffer, followed by washing at 65° C. in a buffer comprising 0.02 to 0.04 M sodium phosphate, pH 7.2, 1% SDS and 1 mM EDTA for between about 30 min to 4 h. Suitable substrate such as nitrocellulose, nylon, polyvinylidene difluoride, or the like can be used as the filter support. A labeled probe, preferably with sufficient specific activity (generally greater than about 108 cpm/μg probe when radioactively labeled, or follow the manufacture instructions when chemical labeling kit is used) is used. In one embodiment, the low salt hybridization buffer comprises, 0.5 to 10% SDS, 0.05 to 0.5 M sodium phosphate. In an exemplary embodiment, where nitrocellulose is used, and the immobilized nucleic acid is DNA immobilized on nitrocellulose, the nitrocellulose with DNA is incubated with a hybridization solution comprising 50% formamide-deionized, 6×SSC, 1% SDS, 0.1% Tween 20 and 100 μg/ml t RNA at 42° C. for 15 minutes. Probe is added and the nitrocellulose is further immobilized at 42° C. for about 12–19 hours. The nitrocellulose is then washed in at least two successive washes at 22° C. followed by stringent washes at 65° C. in a buffer of 0.04M sodium phosphate, pH 7.2, 1% SDS and 1 mM EDTA. Conditions for increasing the stringency of a variety of nucleotide hybridizations are well known in the art.

As discussed additionally herein regarding polynucleotide assays of the invention, for instance, polynucleotides of the invention may be used as a hybridization probe for RNA, cDNA and genomic DNA to isolate full-length cDNAs and genomic clones encoding the sequences of SEQ. ID. NO.:9 and to isolate cDNA and genomic clones of other genes that have a high sequence similarity to SEQ. ID. NO.:9. Such probes generally will comprise at least 15 bases. Preferably, such probes will have at least 30 bases and may have at least 50 bases. Particularly preferred probes will have at least 30 bases and preferably will have 50 bases or less. For example, the coding region of the gene of the invention may be isolated using the known DNA sequence to synthesize an oligonucleotide probe. A labeled oligonucleotide having a sequence complementary to that of a gene of the present invention is then used to screen a library of cDNA, genomic DNA or mRNA to determine to which members of the library the probe hybridizes.

The present invention further relates to polypeptides encoded by the polynucleotides of the invention.

One embodiment of the polypeptides of the invention is a polypeptide comprising an amino acid sequence having at least a 85% identity to amino acids 1 to 12 of SEQ ID NO:10; wherein the polypeptide is capable of forming a functional calcium channel with the other calcium channel subunits, such as α1, β and γ. Preferably, the polypeptide comprising an amino acid sequence having at least a 95% identity to amino acids 1 to 12 of SEQ ID NO:10.

Another embodiment of the polypeptides of the invention is a polypeptide comprising an amino acid sequence having at least a 70% identity to amino acids 1040 to 1090 of SEQ ID NO:10; wherein the polypeptide is capable of forming a functional calcium channel with the other calcium channel subunits, such as α1, β and γ. Preferably, the polypeptide comprising an amino acid sequence having at least a 85% identity to amino acids 1040 to 1090 of SEQ ID NO:10.

Yet another embodiment of the polypeptides of the invention is a polypeptide comprising an amino acid sequence having at least a 85% identity to amino acids 1 to 12 and an amino acid sequence having at least a 70% identity to amino acids 1040 to 1090 of SEQ ID NO:10; wherein the polypeptide is capable of forming a functional calcium channel with the other calcium channel subunits, such as α1, β and γ. Preferably, the polypeptide comprising an amino acid sequence having at least a 95% identity to amino acids 1 to 12 and an amino acid sequence having at least a 85% identity to amino acids 1040 to 1090 of SEQ ID NO:10.

Preferred embodiments of the invention are polypeptides that at least 96% identical over their entire length to the amino acid sequence set out in SEQ ID NO:10. Most preferably, the polypeptide of the present invention includes the polypeptide of SEQ. ID. NO:10.

Recombinant Expression of a Calcium Channel α2δ-4 Subunit

The cloned calcium channel α2δ-4 subunit DNA obtained through the methods described herein may be recombinantly expressed by molecular cloning into an expression vector containing a suitable promoter and other appropriate transcription regulatory elements and transferred into prokaryotic or eukaryotic host cells to produce a recombinant calcium channel α2δ-4 subunit protein. Techniques for such manipulations are fully described in Maniatis, T, et al., supra, and are well known in the art.

Expression vectors are defined herein as DNA sequences that are required for the transcription of cloned copies of genes and the translation of their mRNAs in an appropriate host. Such vectors can be used to express eukaryotic genes in a variety of hosts such as bacteria including *E. coli*, bluegreen algae, plant cells, insect cells, fungal cells including yeast cells, and animal cells.

Specifically designed vectors allow the shuttling of DNA between hosts such as bacteria-yeast or bacteria-animal cells or bacteria-fungal cells or bacteria-invertebrate cells. An appropriately constructed expression vector preferably contains an origin of replication for autonomous replication in host cells, selectable markers, at least one restriction endonuclease recognition site, a potential for high copy number, and active promoters. A promoter is defined as a DNA sequence that directs a RNA polymerase to bind to DNA and initiate RNA synthesis. A strong promoter is one that causes mRNAs to be initiated at high frequency. Expression vectors may include, but are not limited to, cloning vectors, modified cloning vectors, specifically designed plasmids or viruses.

A variety of mammalian expression vectors may be used to express recombinant calcium channel α2δ-4 subunits in mammalian cells. Commercially available mammalian expression vectors which may be suitable for recombinant calcium channel α2δ-4 subunit expression include, but are not limited to, pMAMneo (Clontech), pcDNA3 (Invitrogen), pMC1neo (Stratagene), pXT1 (Stratagene), pSG5 (Stratagene), EBO-pSV2-neo (ATCC 37593) PBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and lZD35 (ATCC 37565).

A variety of bacterial expression vectors may be used to express a recombinant calcium channel α2δ-4 subunit in bacterial cells. Commercially available bacterial expression vectors that may be suitable for recombinant calcium channel α2δ-4 subunit expression include, but are not limited to, pET vectors (Novagen) and pQE vectors (Qiagen).

A variety of fungal cell expression vectors may be used to express a recombinant α2δ-4 calcium channel subunit in fungal cells such as yeast. Commercially available fungal cell expression vectors suitable for recombinant calcium channel α2δ-4 subunit expression include, but are not limited, to pYES2 (Invitrogen) and Pichia expression vectors (Invitrogen).

A variety of insect cell expression vectors may be used to express a recombinant calcium channel α2δ-4 subunit in insect cells. Commercially available insect cell expression vectors suitable for the recombinant expression of a calcium channel α2δ-4 subunit include, but are not limited to pBlueBacII (Invitrogen).

DNA encoding a calcium channel α2δ-4 subunit may be cloned into an expression vector for expression in a recombinant host cell. Recombinant host cells may be prokaryotic or eukaryotic, including, but not limited to, bacteria such as *E. coli*, fungal cells such as yeast, mammalian cells including, but not limited to, cell lines of human, bovine, porcine, monkey and rodent origin, and insect cells including, but not limited to, *drosophila* and silkworm derived cell lines. Cell lines derived from mammalian species that are commercially available and can be used in this invention include, but are not limited to, CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171), L-cells, and HEK-293 (ATCC CRL1573).

The expression vector may be introduced into host cells via any one of a number of techniques including, but not limited to, transformation, transfection, protoplast fusion, lipofection, and electroporation. The expression vector-containing cells are clonally propagated and individually analyzed to determine whether they produce calcium channel α2δ-4 subunit protein. The identification of calcium channel α2δ-4 subunit expressing host cell clones may be performed using antibody recognizing the calcium channel α2δ-4 subunit or alternatively, cells expressing the subunit can be identified based on the presence of host cell-associated calcium channel α2δ-4 subunit activity.

Expression of calcium channel α2δ-4 subunit DNA may also be performed using in vitro produced synthetic mRNA. Synthetic mRNA or mRNA isolated from calcium channel α2δ-4 subunit producing cells can be efficiently translated in various cell-free systems including, but not limited to, wheat germ extracts and reticulocyte extracts. mRNA can also be translated in cell based systems by, for example, microinjection into frog oocytes.

To determine the calcium channel α2δ-4 subunit DNA sequence(s) that yields optimal levels of calcium channel α2δ-4 subunit activity and/ calcium channel α2δ-4 subunit protein, calcium channel α2δ-4 subunit DNA molecules can be constructed. One construct contemplated for use is the full-length open reading frame of the calcium channel α2δ-4 subunit cDNA encoding a protein of 1090 amino acids and corresponding to approximately base 189 to approximately base 3472 of SEQ ID NO:9 (these numbers correspond to the first nucleotide of the first methionine and last nucleotide before the first stop codon). Other constructs are those that contain portions of the cDNA that encode a calcium channel α2δ-4 subunit protein. All constructs can be designed to contain none, all or portions of the 5' or the 3' untranslated region of a calcium channel α2δ-4 subunit cDNA. Calcium channel α2δ-4 subunit activity and levels of protein expression can be determined following the introduction, both singly or in combination, of these constructs into appropriate host cells. Once the calcium channel α2δ-4 subunit DNA cassette yielding optimal expression in transient assays has been identified, this calcium channel α2δ-4 subunit DNA construct can be transferred to a variety of expression vectors for expression in host cells including, but not limited to, mammalian cells, baculovirus-infected insect cells, *E. coli*, and the yeast *S. cerevisiae*.

Production and Purification of A Calcium Channel α2δ-4 Subunit Protein

The present invention provides methods of produce substantially purified polypeptide of the invention. As used herein, the term "substantially purified" means that the protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

As used herein, "recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

In one embodiment, the polypeptide can be isolated from cells or tissue sources that express it naturally by an appropriate purification scheme using standard protein purification techniques. In another embodiment, polypeptides of the invention are produced by recombinant DNA techniques. Alternatively, a polypeptide of the invention can be synthesized in an in vitro translation and/or transcription system. Further alternatively, a polypeptide of the invention can be synthesized chemically using standard peptide synthesis techniques. Following expression of a calcium channel α2δ-4 subunit of this invention in a recombinant host cell, the calcium channel $\alpha_2\delta$-4 subunit protein may be recovered to provide a purified calcium channel $\alpha_2\delta$-4 subunit in active form. Several calcium channel $\alpha_2\delta$-4 subunit purification procedures are available and suitable for use. For example, as discussed above, a recombinant calcium channel $\alpha_2\delta$-4 subunit may be purified from cell lysates and extracts or from conditioned culture medium using various combinations of or individual application of salt fractionation, ion exchange chromatography, size exclusion chromatography, hydroxylapatite adsorption chromatography and hydrophobic interaction chromatography, lectin chromatography, and antibody/ligand affinity chromatography.

Recombinant calcium channel $\alpha_2\delta$-4 subunits can be separated from other cellular proteins using an immunoaffinity column made with monoclonal or polyclonal antibodies monospecific for a full length nascent calcium channel $\alpha_2\delta$-4 subunit, specific for polypeptide fragments of a calcium channel $\alpha_2\delta$-4 subunit or specific for calcium channel $\alpha_2\delta$-4 subunit subunits. Once the affinity resin is prepared and loaded onto a column, the affinity resin is equilibrated in a suitable buffer, for example phosphate buffered saline (pH 7.3). The cell culture supernatants or cell extracts containing the calcium channel $\alpha_2\delta$-4 subunit or subunits of the $\alpha_2\delta$-4calcium channel are slowly passed through the column. The column is washed with the buffer until the optical density ($A_{280}$) falls to background, next the protein is eluted by changing the buffer condition, such as by lowering the pH using a buffer such as 0.23 M glycine-HCl (pH 2.6). The purified calcium channel $\alpha_2\delta$-4 subunit protein is then dialyzed against a suitable buffer such as phosphate buffered saline.

Polypeptides of the invention may also be produced using an in vitro translation and/or transcription system. Such methods are known to those skilled in the art. For example, synthetic α2δ-4 mRNA or mRNA isolated from calcium channel α2δ-4 producing cells can be efficiently translated in various cell-free systems, including but not limited to wheat germ extracts and reticulocyte extracts. Alternatively, the coding sequence of α2δ-4 cDNA can be cloned under the control of a T7 promoter. Then, using this construct as the template, α2δ-4 subunit protein can be produced in an in vitro transcription and translation system, the TNT T7 coupled Reticulocyte Lysate System, which is commercially available from Promega.

Polypeptides of the invention may also be produced by chemical synthesis, such as solid phase peptide synthesis on an automated peptide synthesizer, using known amino acid sequences or amino acid sequences derived from the DNA sequence of the genes of interest. Such methods are known to those skilled in the art.

Antibodies for Polypeptides of the Present Invention

Another aspect of the invention pertains to antibodies directed against a polypeptide of the invention. The term "antibody" as used herein refers to immunoglobulin molecules and immunologically active portions of immunoglobulin molecules, i.e., molecules that contain an antigen binding site which specifically binds an antigen, such as a polypeptide of the invention, e.g., an epitope of a polypeptide of the invention. A molecule which specifically binds to a given polypeptide of the invention is a molecule which binds the polypeptide, but does not substantially bind other molecules in a sample, e.g., a biological sample, which naturally contains the polypeptide. Examples of immunologically active portions of immunoglobulin molecules include F(ab) and F(ab')2 fragments which can be generated by treating the antibody with an enzyme such as pepsin.

The invention provides polyclonal and monoclonal antibodies. The term "monoclonal antibody" or "monoclonal antibody composition", as used herein, refers to a population of antibody molecules that contain only one species of an antigen binding site capable of immunoreacting with a particular epitope. The term "polyclonal antibody" refers to antibodies directed against a polypeptide or polypeptides of the invention capable of immunoreacting with more than one epitopes. Particularly preferred polyclonal antibody preparations are ones that contain only antibodies directed against a polypeptide or polypeptides of the invention.

The term "antigen" as used herein refers to a molecule containing one or more epitopes that will stimulate a host's immune system to make a humoral and/or cellular antigen-specific response. The term is also used herein interchangeably with "immunogen."

The term "epitope" as used herein refers to the site on an antigen or hapten to which a specific antibody molecule binds. The term is also used herein interchangeably with "antigenic determinant" or "antigenic determinant site."

An isolated polypeptide of the invention, or a fragment thereof, can be used as an immunogen to generate antibodies using standard techniques for polyclonal and monoclonal antibody preparation. The full-length polypeptide or protein can be used or, alternatively, the invention provides antigenic peptide fragments for use as immunogens. The antigenic peptide of a protein of the invention comprises at least 8 (preferably 10, 15, 20, or 30) amino acid residues of the amino acid sequence of SEQ ID NO:10 and encompasses an epitope of the protein such that an antibody raised against the peptide forms a specific immune complex with the protein. Preferred epitopes encompassed by the antigenic peptide are regions that are located on the surface of the protein, e.g., hydrophilic regions of the proteins of the invention. Hydrophobic or hydrophilic regions on a protein can be identified using hydrophobicity plotting software programs.

An immunogen typically is used to prepare antibodies by immunizing a suitable subject, (e.g., rabbit, goat, mouse or other mammal). An appropriate immunogenic preparation can contain, for example, recombinantly expressed or chemically synthesized polypeptide. The preparation can further include an adjuvant, such as Freund's complete or incomplete adjuvant, or similar immunostimulatory agent. Particularly preferred immunogen compositions are those that contain no other human proteins such as, for example, immunogen compositions made using a non-human host cell for recombinant expression of a polypeptide of the invention. In such a manner, the only human epitope or epitopes recognized by the resulting antibody compositions raised against this immunogen will be present as part of a polypeptide or polypeptides of the invention.

Polyclonal antibodies can be raised by immunizing a suitable subject animals such as mice, rats, guinea pigs, rabbits, goats, horses and the like, with rabbits being preferred, with a polypeptide of the invention as an immunogen either with or without an immune adjuvant. Preimmune serum is collected prior to the first immunization. Each animal receives between about 0.001 mg and about 1000 mg of polypeptide of the invention associated with or without an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of the polypeptide in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunizaiton. Those animals receiving booster injections are generally given an equal amount of the antigen in Freund's incomplete adjuvant by the same route. Booster injections are given at about three-week intervals until maximal titers are obtained. At about 7 days after each booster immunization or about weekly after a single immunization, the animals are bled, the serum collected, and aliquots are stored at about −20° C.

Monoclonal antibodies (mAb) reactive with α2δ-4 calcium channel subunit are prepared by immunizing inbred mice, preferably Balb/c, with polypeptide of the invention. The mice are immunized by the IP or SC route with about 0.001 mg to about 1.0 mg, preferably about 0.1 mg, of polypeptide of the invention in about 0.1 ml buffer or saline incorporated in an equal volume of an acceptable adjuvant, as discussed above. Freund's adjuvant is preferred, with Freund's complete adjuvant being used for the initial immunization and Freund's incomplete adjuvant used thereafter. The mice receive an initial immunization on day 0 and are rested for about 2 to about 30 weeks. Immunized mice are given one or more booster immunizations of about 0.001 to about 1.0 mg of polypeptide of the invention in a buffer solution such as phosphate buffered saline by the intravenous (IV) route. Lymphocytes, from antibody positive mice, preferably spleenic lymphocytes, are obtained by removing spleens from immunized mice by standard procedures known in the art. Hybridoma cells are produced by mixing the splenic lymphocytes with an appropriate fusion partner, preferably myeloma cells, under conditions that will allow the formation of stable hybridomas. Fusion partners may include, but are not limited to: mouse myelomas P3/NS1/Ag 4-1; MPC-11; S-194 and Sp2/0, with Sp2/0 being generally preferred. The antibody producing cells and myeloma cells are fused in polyethylene glycol, about 1000 mol. wt., at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using polypeptide of the invention as the antigen. The culture fluids are also tested in the Ouchterlony precipitation assay to determine the isotype of the mAb. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973 or by the technique of limited dilution.

Monoclonal antibodies are produced in vivo by injection of pristane primed Balb/c mice, approximately 0.5 ml per mouse, with about 1×106 to about 6×106 hybridoma cells at least about 4 days after priming. Ascites fluid is collected at approximately 8–12 days after cell transfer and the monoclonal antibodies are purified by techniques known in the art.

Monoclonal Ab can also be produced In vitro by growing the hydridoma in tissue culture media well known in the art. High density in vitro cell culture may be conducted to produce large quantities of mAbs using hollow fiber culture techniques, air lift reactors, roller bottle, or spinner flasks culture techniques well known in the art. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. The antibody molecules can be isolated from the mammal (e.g., from the blood) or culture cells and further purified by well-known techniques, such as protein A chromatography to obtain the IgG fraction. Alternatively, antibodies specific for a protein or polypeptide of the invention can be selected for (e.g., partially purified) or purified by, e.g., affinity chromatography. For example, a recombinantly expressed and purified (or partially purified) protein of the invention is produced as described herein, and covalently or non-covalently coupled to a solid support such as, for example, a chromatography column. The column can then be used to affinity purify antibodies specific for the proteins of the invention from a sample containing antibodies directed against a large number of different epitopes, thereby generating a substantially purified antibody composition, i.e., one that is substantially free of contaminating antibodies. By a substantially purified antibody composition is meant, in this context, that the antibody sample contains at most only 30% (by dry weight) of contaminating antibodies directed against epitopes other than those on the desired protein or polypeptide of the invention, and preferably at most 20%, yet more preferably at most 10%, and most preferably at most 5% (by dry weight) of the sample is contaminating antibodies. A purified antibody composition means that at least 99% of the antibodies in the composition are directed against the desired protein or polypeptide of the invention.

Additionally, recombinant antibodies, such as chimeric and humanized monoclonal antibodies, comprising both human and non-human portions, which can be made using standard recombinant DNA techniques, are within the scope of the invention. A chimeric antibody is a molecule in which different portions are derived from different animal species, such as those having a variable region derived from a murine mAb -and a human immunoglobulin constant region (See, e.g., Cabilly et al., U.S. Pat. No. 4,816,567; and Boss et al., U.S. Pat. No. 4,816,397,). Humanized antibodies are antibody molecules from non-human species having one or more complementarily determining regions (CDRs) from the non-human species and a framework region from a human immunoglobulin molecule (See, e.g., Queen, U.S. Pat. No. 5,585,089,). Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125, 023; Better et al. (1988) Science 240:1041–1043; Liu et al. (1987) Proc. Natl. Acad. Sci. USA 84:3439–3443; Liu et al. (1987) J Immunol. 139:3521–3526; Sun et al. (1987) Proc. Natl. Acad. Sci. USA 84:214–218; Nishimura et al. (1987) Canc. Res. 47:999–1005; Wood et al. (1985) Nature 314:446–449; and Shaw et al. (1988) J. Natl. Cancer Inst. 80:1553–1559); Morrison (1985) Science 229:1202–1207; Oi et al. (1986) BiolTechniques 4:214; U.S. Pat. No. 5,225,539; Jones et al. (1986) Nature 321:552–525; Verhoeyan et al. (1988) Science 239:1534; and Beidler et al. (1988) J Immunol. 141:4053–4060.

Completely human antibodies are particularly desirable for therapeutic treatment of human patients. Such antibodies can be produced, for example, using transgenic mice which are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA and IgE antibodies. For an overview of this technology for producing human antibodies, see Lonberg and Huszar (1995, Int. Rev. Immunol. 13:65–93). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806. In addition, companies such as Abgenix, Inc. (Fremont, Calif.), can be engaged to provide human antibodies directed against a selected antigen using technology similar to that described above.

Completely human antibodies which recognize a selected epitope can be generated using a technique referred to as "guided selection". In this approach a selected non-human monoclonal antibody, e.g., a mouse antibody, is used to guide the selection of a completely human antibody recognizing the same epitope (Jespers et al. (1994) Bioltechnology 12:899–903).

An antibody directed against a polypeptide of the invention (e.g., monoclonal antibody) can be used to isolate the polypeptide by standard techniques, such as affinity chromatography or immunoprecipitation. Moreover, such an antibody can be used to detect the protein (e.g., in a cellular lysate or cell supernatant) in order to evaluate the abundance and pattern of expression of the polypeptide. The antibodies can also be used diagnostically to monitor protein levels in tissue as part of a clinical testing procedure, e.g., to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetyleholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, 131I, 35S or 3H. Further, an antibody (or fragment thereof) can be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, I-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCN-LJ), cyclothosphamide, busulfan, dibromomannitol, streptozotocin, mitomycin C, and cis-dichlorodiamine platinum (11) (DDP) cisplatin), anthracyclines (e.g., daunorubicin (formerly daunomycin) and doxorabicin), antibiotics (e.g., dactinomycin (formerly actinomycin), bleomycin, mithramycin, and anthramycin (AMC)), and anti-rmitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha.-interferon, beta.-interferon, nerve growth factor, platelet derived growth factor, tissue plasminogen activator; or, biological response modifiers such as, for example, lymphokines, interleukin-1 ("IL-I"), interleukin-2 ("IL-211), interleukin-6 ("IL-6"), granulocyte monocyte colony stimulating factor ("GM-CSF"), granulocyte colony stimulating factor ("G-CSF"), or other growth factors. Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980. It is readily apparent to those skilled in the art that the above described methods for producing polyclonal or monoclonal antibodies may be utilized to produce antibodies specific for α2δ-4 calcium channel subunit fragments, or full-length nascent α2δ-4 calcium channel subunit, or the individual α2δ-4 calcium channel subunit. It is also apparent to those skilled in the art that antibodies may be generated that inhibit normal function of calcium channel comprising the α2δ-4 calcium channel subunit.

Preferably, the invention provides substantially purified antibodies or fragment thereof, which specifically bind to a polypeptide with amino acid sequence substantially similar to the amino acids 1 to 12 or 1040 to 1090 of SEQ ID NO:10. In various embodiments, the substantially purified antibodies of the invention, or fragments thereof, can be human, non-human, chimeric and/or humanized antibodies. Such antibodies of the invention can be, but are not limited to, goat, mouse, sheep, horse, chicken, rabbit, or rat antibodies. In addition, such antibodies of the invention can be polyclonal antibodies or monoclonal antibodies.

Any of the antibodies of the invention can be conjugated to a therapeutic moiety or to a detectable substance. Non-limiting examples of detectable substances that can be conjugated to the antibodies of the invention are an enzyme, a prosthetic group, a fluorescent material, a luminescent material, a bioluminescent material, and a radioactive material.

The invention also provides a kit containing an antibody of the invention conjugated to a detectable substance, and instructions for use. Still another aspect of the invention is a pharmaceutical composition comprising an antibody of the invention and a pharmaceutically acceptable carrier. In preferred embodiments, the pharmaceutical composition contains an antibody of the invention, a therapeutic moiety, and a pharmaceutically acceptable carrier.

Identification of a Disease or Disorder Associated with Defective α2δ-4 Calcium Channel Subunit One aspect of the present invention relates to a method to identify a disease or disorder associated with defective α2δ-4 calcium channel subunit in a subject. Alternatively, these methods can be used to identify a variation in the nucleic acid or amino acid sequence of the α2δ-4 calcium channel subunit or to detect altered activity of an α2δ-4 calcium channel subunit, particularly those forming a calcium channel with the calcium channel subunits.

As used herein, the term "a disease or disorder associated with defective α2δ-4 calcium channel subunit" refers to a disease or disorder characterized by aberrant expression or activity of a α2δ-4 calcium channel subunit. Said disease or disorder includes, but is not limited to, a member selected from the group consisting of: seizure-related syndromes, epilepsy, migraine, ataxia, vestibular defects, chronic pain, neuropathic pain, mood, sleep interference, anxiety, ALS, multiple sclerosis, mania, tremor, parkinsonism, substance abuse/addiction syndromes, depression, cancer, and inflammation.

The term "defective α2δ-4 calcium channel subunit' as used herein refers to aberrant expression or activity of a α2δ-4 calcium channel subunit caused by one or more of the following conditions: 1) increased α2δ-4 expression; 2) decreased α2δ-4 expression; 3) changes in α2δ-4 subunit activity causing an increased or decreased ionic conductivity in a calcium channel comprising the α2δ-4 subunit ; or 4) presence of mutations in α2δ-4 gene which significantly affects the integrity of the gene.

As used herein, "mutation in α2δ-4 gene which significantly affects the integrity of the gene", include, but are not limited to: 1) a deletion of one or more nucleotides from the gene; 2) an addition of one or more nucleotides to the gene; 3) a substitution of one or more nucleotides of the gene; 4)

a chromosomal rearrangement of the gene; 5) an alteration in the level of a messenger RNA transcript of the gene; 6) an aberrant modification of the gene, such as of the methylation pattern of the genomic DNA; 7) the presence of a non-wild type splicing pattern of a messenger RNA transcript of the gene; 8) a non-wild type level of a the protein encoded by the gene; 9) an allelic loss of the gene; and 10) an inappropriate post-translational modification of the protein encoded by the gene.

The term "subject" as used herein, refers to an animal, preferably a mammal, most preferably a human, who has been the object of treatment, observation or experiment.

The term "control individual" as used herein, refers to the same animal as that of the subject to whom it compares with, who does not have a disease or disorder associated with defective α2δ-4 calcium channel subunit.

An exemplary method for diagnosing a disease or disorder associated with defective α2δ-4 calcium channel subunit in a subject comprising obtaining a biological sample from the subject and the control individual; assaying the amount of α2δ-4 mRNA or protein in the biological samples; and comparing the assaying results obtained from the subject and the control individual, wherein a significant change in α2δ-4 mRNA or protein levels in the subject relative to that of the control individual indicates that the subject is affiliated with a disease or disorder associated with defective α2δ-4 calcium channel subunit.

The term "biological sample" as used herein is intended to include tissues, cells and biological fluids isolated from a subject, as well as tissues, cells and fluids present within a subject. In one embodiment, the biological sample contains protein molecules from the subject. The protein molecules may or may not remain their native biological activities. In another embodiment, the biological sample contains nucleic acid including genomic DNA, and/or mRNA molecules from the test subject or from the subject. In yet another embodiment, the biological sample contains both proteins and nucleic acid molecules.

As used herein, "a significant change" refers to either an increase or decrease in the amount of α2δ-4 mRNA or protein or $Ca^{2+}$ current density, which is measured reproducibly, or a mutation in α2δ-4 gene which significantly affects the integrity of the α2δ-4 gene. Generally, a significant decrease in the amount of α2δ-4 mRNA or protein or $Ca^{2+}$ current density is at least 10% to 20%, preferably by at least 30% to 50%, more preferably by at least 60% to 80%, and most preferably by at least 90% to 100%. Typically, a significant increase in the amount of α2δ-4 mRNA or protein or $Ca^{2+}$ current density is at least 20% to 200%, preferably by at least 400% to 800%, and most preferably by at least 1,000%.

The mRNA or protein level of α2δ-4 in the biological samples can be measured by contacting the sample with a compound or an agent capable of detecting the mRNA or protein of α2δ-4, respectively.

A preferred agent for detecting α2δ-4 mRNA is a labeled nucleic acid probe capable of hybridizing specifically to the mRNA. The nucleic acid probe can be, for example, a full-length cDNA, such as the nucleic acid of SEQ ID NO:9, or a portion thereof, such as an oligonucleotide of at least 15, 30, 50, 100, 250 or 500 nucleotides in length and sufficient to specifically hybridize under stringent conditions to a α2δ-4 mRNA.

A preferred agent for detecting a α2δ-4 polypeptide is an antibody capable of binding specifically to the polypeptide, preferably a labeled antibody with a detectable label. Antibodies can be polyclonal, or more preferably, monoclonal. An intact antibody, or a fragment thereof (e.g., Fab or F(ab')) can be used.

The term "labeled", with regard to the nuclei acid probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Protein and mRNA in biological samples can be assayed in vitro as well as in vivo. For example, in vitro techniques for detection of mRNA include Northern hybridizations, DNA microarray, and RT-PCR. In vitro techniques for detection of a polypeptide include enzyme linked immunosorbent assays (ELISAs), Western blots, RIA and immunoprecipitations and immunofluorescence. In vivo techniques for detection of mRNAs include transcriptional fusion described infra. In addition, mRNA or proteins can also be assayed by in-situ hybridization and immunohistochemistry (to localized messenger RNA and protein to specific subcellular compartments and/or within neuropathological structures associated with the disease).

The invention also encompasses kits for diagnosing and monitoring the progression of treatment of neuropathic pain. Such a kit would comprise a labeled compound or agent capable of detecting α2δ-4 protein or mRNAs specifically (e.g., an antibody which binds specifically to α2δ-4 polypeptide or an oligonucleotide probe which binds to mRNA encoding the α2δ-4 polypeptide) and a means for detection such as labeled antigen or enzyme substrates or the like. The kits can also include instructions for observing that the subject is suffering from neuropathic pain if the amount of the polypeptide or mRNA encoding the polypeptide is above or below a normal level. For antibody-based kits, the kit can comprise, for example: (1) a first antibody (e.g., attached to a solid support) which binds to a α2δ-4 protein; and, optionally; (2) a second, different antibody which binds to either the polypeptide or the first antibody and is conjugated to a detectable agent; and (3) a purified α2δ-4 protein as positive control.

For oligonucleotide-based kits, the kit can comprise, for example: (1) an oligonucleotide, e.g., a detectably labeled oligonucleotide, which hybridizes to SEQ ID NO:9 under stringent hybridization condition; and (2) a pair of primers useful for amplifying a nucleic acid molecule of SEQ ID NO:9 or portions thereof. The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of the polypeptide.

Another exemplary method for diagnosing a disease or disorder associated with defective α2δ-4 calcium channel subunit in a subject, comprising obtaining a biological sample from the subject and the control individual; assaying the amount of ion flux through the calcium channel in the biological samples; and comparing the assaying results obtained from the subject and the control individual, wherein a significant change in ion flux through the calcium channel in the subject relative to that of the control individual indicates that the subject is affiliated with a disease or disorder associated with defective α2δ-4 calcium channel subunit.

A variety of assay methods can be used to determine the effect of the compound to increase or decrease the flux of ions through the calcium channel, which include but are not limited to, voltage-clamp technique, radioisotope flux assays, and fluorescence assays using voltage-sensitive dyes (See, e.g., Vestergarrd-Bogind et al., J. Membrane Biol., 88: 67–75, 1988; Daniel et al., J. Pharmacol. Meth., 25:185–193, 1991; Holevinsky et al., J. Membrane Biology, 137: 59–70, 1994). Such assays are known to those skilled in the art. One exemplary assay for $Ca^{2+}$ flux is described in Example 14.

Yet another exemplary method for diagnosing a disease or disorder associated with defective α2δ-4 calcium channel subunit in a subject or identifying variations in an α2δ-4 calcium channel subunit or α2δ-4 calcium channel subunit activity preferably comprises obtaining a biological sample from a subject; assaying the amount of α2δ-4 nucleic acid or polypeptide in the sample or measuring the ionic flux through a calcium channel or identifying mutations in nucleic acid encoding a α2δ-4 calcium channel subunit and comparing results from the assaying portion of the method with a biological sample from a control subject. Changes in a sample relative to a control indicate defects that can be associated with a disease.

There are a large number of assay techniques known in the art which can be used for detecting lesions in a gene. In certain embodiments, detection of the lesion involves the use of a probe/primer in a polymerase chain reaction (PCR), such as anchor PCR or RACE PCR, or, alternatively, in a ligation chain reaction (LCR) (see, e.g., Landegran et al. (1988) Science 241:1077–1080; and Nakazawa et al. (1994) Proc. Natl. Acad. Sci. USA 91:360–364), the latter of which can be particularly useful for detecting point mutations in a gene (see, e.g., Abravaya et al. (1995) Nucleic Acids Res. 23:675–682). In an alternative embodiment, mutations in a selected gene from a sample cell can be identified by alterations in restriction enzyme cleavage patterns. In other embodiments, genetic mutations can be identified by hybridizing a sample and control nucleic acids, e.g., DNA or RNA, to high density arrays containing hundreds or thousands of oligonucleotides probes (Cronin et al. (1996) Human Mutation 7:244–255). In yet another embodiment, any of a variety of sequencing reactions known in the art can be used to directly sequence the selected gene and detect mutations by comparing the sequence of the sample nucleic acids with the corresponding wild-type (control) sequence. In other embodiments, alterations in electrophoretic mobility will be used to identify mutations in genes.

Treating a Disease or Disorder Associated with Defective α2δ-4 Calcium Channel Subunit The present invention additionally relates to a method of treating a disease or disorder associated with defective α2δ-4 calcium channel subunit.

In one embodiment, calcium channel α2δ-4 subunit antisense therapy may be used to decrease the expression of a calcium channel α2δ-4 subunit in the cells of target organisms. Calcium channel α2δ-4 subunit antisense therapy may be particularly useful for the treatment of diseases where it is beneficial to decrease calcium channel α2δ-4 subunit activity.

The principle of antisense based strategies is based on the hypothesis that sequence-specific suppression of gene expression can be achieved by intracellular hybridization between mRNA and a complementary antisense species. The formation of a hybrid RNA duplex may then interfere with the processing/transport/translation and/or stability of the target α2δ-4 mRNA. Hybridization is required for the antisense effect to occur. Antisense strategies may use a variety of approaches including the use of antisense oligonucleotides, injection of antisense RNA and transfection of antisense RNA expression vectors. Phenotypic effects induced by antisense effects are based on changes in criteria such as protein levels, protein activity measurement, and target mRNA levels. Multidrug resistance is a useful control to study molecular events associated with phenotypic changes due to antisense effects, since the multidrug resistance phenotype can be established by expression of a single gene mdr1(MDR gene) encoding for P-glycoprotein.

An antisense nucleic acid can be complementary to an entire coding strand of a α2δ-4 gene, or to only a portion thereof. An antisense nucleic acid molecule can also be complementary to all or part of a non-coding region of the coding strand of a α2δ-4 gene. The non-coding regions ("5' and 3' untranslated regions") are the 5' and 3' sequences which flank the coding region and are not translated into amino acids. Preferably, the non-coding region is a regulatory region for the transcription or translation of the α2δ-4 channel gene. The term "regulatory region" or "regulatory sequence" is intended to include promoters, enhancers and other expression control elements (e.g., polyadenylation signals, and ribosome binding site (for bacterial expression) and, an operator). Such regulatory sequences are described and can be readily determined using a variety of methods known to those skilled in the art (see for example, in Goeddel, Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences).

An antisense oligonucleotide can be, for example, about 15, 25, 35, 45 or 65 nucleotides or more in length taken from the complementary sequence of SEQ ID NO:9. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxytnethylaminomethyl-2-thiouridine, 5-carboxymethylaminomethyluracil, dihydrouracil, beta-D-galactosylqueosine, inosine, N6-isopentenyladenine, I-methylguanine, 1-methylinosine, 2,2-dimethylguanine, 2-methyladenine, 2-methylguanine, 3-methylecytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. An antisense nucleic acid molecule can be a CC-anomeric nucleic acid molecule. A CC-anomeric nucleic acid molecule forms specific double-stranded hybrids with complementary RNA in which, contrary to the usual P-units, the strands run parallel to each other (Gaultier et al. (1987) Nucleic Acids Res. 15:6625–664 1). The antisense nucleic acid molecule can also comprise a 2'-o-methylribonucleotide (Inoue et al. (1987) Nucleic Acids Res. 15:6131–6148) or a chimeric RNA-DNA analogue (Inoue et al. (1987) FEBS Lett. 215:327–330).

Alternatively, the antisense nucleic acid can also be produced biologically using an expression vector into which a nucleic acid has been subcloned in an antisense orientation (i.e., RNA transcribed from the inserted nucleic acid will be of an antisense orientation to a target nucleic acid of interest). That is, a DNA molecule is operably linked to a regulatory sequence in a manner which allows for expression (by transcription of the DNA molecule) of an RNA molecule which is antisense to the mRNA encoding a α2δ-4 calcium subunit. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (Reviews—Trends in Genetics, Vol. I(I) 1986).

Typically, antisense nucleic acid administered to a subject by microinjection, liposome encapsulation or generated in situ by expression from vectors harboring the antisense sequence. The antisense nucleic acid can be ligated into viral vectors that mediate transfer of the antisense nucleic acid by infection of recipient host cells. Suitable viral vectors include retrovirus, adenovirus, adeno-associated virus, herpes virus, vaccinia virus, polio virus and the like. Alternatively, antisense nucleic acids can be transferred into cells for gene therapy by non-viral techniques including receptor-mediated targeted nuclei acid transfer using ligand-nucleic acid conjugates or adenovirus-ligand-nucleic acid conjugates, lipofection membrane fusion or direct microinjection.

Once inside the cell, antisense nucleic acid molecules hybridize with or bind to cellular mRNA and/or genomic DNA encoding a α2δ-4 protein to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In another embodiment, calcium channel α2δ-4 subunit gene therapy may be used to introduce a calcium channel α2δ-4 subunit into the cells of target organisms. Calcium channel α2δ-4 subunit gene therapy may be particularly useful for the treatment of diseases where it is beneficial to elevate calcium channel α2δ-4 subunit activity.

The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy uses vectors such as adenovirus, retroviruses, vaccinia virus, bovine papilloma virus, and herpes virus such as Epstein-Barr virus. Gene transfer could also be achieved using non-viral means requiring infection in vitro. This would include calcium phosphate, DEAE dextran, electroporation, and protoplast fusion. Targeted liposomes may also be potentially beneficial for delivery of DNA into a cell. For example, DNA molecule encoding the α2δ-4 protein, is first cloned into a retroviral vector. The expression of α2δ-4 protein from the vector is driven from its endogenous promoter or from the retroviral long terminal repeat or from a promoter specific for certain target cells. The vector is then introduced into a subject in need of to successfully express α2δ-4 protein proteins in the target cells. The gene must be delivered to those cells in a form in which it can be taken up and code for sufficient protein to provide effective function. Retroviral vectors can be used as a gene delivery vector for Gene therapy especially because of their high efficiency of infection and stable integration and expression. Alternatively, calcium channel α2δ-4 subunit DNA can be transferred into cells for gene therapy by non-viral techniques including receptor-mediated targeted DNA transfer using ligand-DNA conjugates or adenovirus-ligand-DNA conjugates, lipofection membrane fusion or direct microinjection. These procedures and variations thereof are suitable for ex vivo as well as in vivo calcium channel α2δ-4 subunit gene therapy. Protocols for molecular methodology of gene therapy suitable for use with the calcium channel α2δ-4 subunit gene is described in Gene Therapy Protocols, edited by Paul D. Robbins, Human press, Totowa N.J., 1996.

Identification of Compounds that are Useful for Treating a Disease or Disorder Associated with a Defective α2δ-4 Calcium Channel Subunit The invention further provides efficient methods of identifying compounds that are useful for treating disease or disorder associated with a defective α2δ-4 calcium channel subunit or to identify variations in α2δ-4 calcium channel subunits or subunit activity. Generally, the methods involve identifying compounds which activate or repress the expression of an α2δ-4 calcium channel subunit, or increase or decrease Ca$^{2+}$ flux through a calcium channel comprising a α2δ-4 calcium channel subunit.

The compound identification methods can be in conventional laboratory format or adapted for high throughput. The term "high throughput" refers to an assay design that allows easy analysis of multiple samples simultaneously, and capacity for robotic manipulation. Another desired feature of high throughput assays is an assay design that is optimized to reduce reagent usage, or minimize the number of manipulations in order to achieve the analysis desired. Examples of assay formats include 96-well or 384-well plates, levitating droplets, and "lab on a chip" microchannel chips used for liquid handling experiments. It is well known by those in the art that as miniaturization of plastic molds and liquid handling devices are advanced, or as improved assay devices are designed, that greater numbers of samples may be performed using the design of the present invention.

Candidate compounds encompass numerous chemical classes, although typically they are organic compounds. Preferably, they are small organic compounds, i.e., those having a molecular weight of more than 50 yet less than about 2500. Candidate compounds comprise functional chemical groups necessary for structural interactions with polypeptides, and typically include at least an amine, carbonyl, hydroxyl or carboxyl group, preferably at least two of the functional chemical groups and more preferably at least three of the functional chemical groups. The candidate compounds can comprise cyclic carbon or heterocyclic structure and/or aromatic or polyaromatic structures substituted with one or more of the above-identified functional groups. Candidate compounds also can be biomolecules such as peptides, saccharides, fatty acids, sterols, isoprenoids, purines, pyrimidines, derivatives or structural analogs of the above, or combinations thereof and the like. Where the compound is a nucleic acid, the compound typically is a DNA or RNA molecule, although modified nucleic acids having non-natural bonds or subunits are also contemplated.

Candidate compounds are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Candidate compounds can also be obtained using any of the numerous approaches in combinatorial library methods known in the art, including: biological libraries; spatially addressable parallel solid phase or solution phase libraries: synthetic library methods requiring deconvolution; the "one-bead one-compound" library method; and synthetic library methods using affinity chromatography selection (Lam (1997) Anticancer Drug Des. 12:145). Alternatively, libraries of natural compounds in the form of bacterial, fungal, plant and animal extracts are available or readily produced. Additionally, natural and synthetically produced libraries and compounds can be readily modified through conventional chemical, physical, and biochemical means.

Further, known pharmacological agents may be subjected to directed or random chemical modifications such as acylation, alkylation, esterification, amidification, etc. to produce structural analogs of the agents. Candidate compounds can be selected randomly or can be based on existing compounds which bind to and/or modulate the function of α2δ-4 channels. Therefore, a source of candidate agents are libraries of molecules based on the known calcium channel activators or inhibitors, in which the structure of the compound is changed at one or more positions of the molecule to contain more or fewer chemical moieties or different chemical moieties. The structural changes made to the molecules in creating the libraries of analog activators/inhibitors can be directed, random, or a combination of both directed and random substitutions and/or additions. One of ordinary skill in the art in the preparation of combinatorial libraries can readily prepare such libraries based on the existing calcium channel activators/inhibitors.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease inhibitors, nuclease inhibitors, antimicrobial agents, and the like may also be used.

Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994). J Med. Chem. 37:2678. Libraries of compounds may be presented in solution (e.g., Houghten (1992) Biotechniques 13:412–421), or on beads (Lam (1991) Nature 354:82–84), chips (Fodor (1993) Nature 364:555–556), bacteria (U.S. Pat. No. 5,223,409), spores (U.S. Pat. No. 5,571, 698), plasmids (Cull et al. (1992) Proc. Natl. Acad. Sci. USA 89:1865–1869) or phage (see e.g., Scott and Smith (1990) Science 249:3 86–390).

As used herein, "compounds that activate or repress (i.e., increase or decrease) the α2δ-4 protein expression" include compounds that activate or repress α2δ-4 gene transcription and/or translation. The invention provides a method of identifying such a compound, comprising the steps of contacting a compound with a host cell comprising a regulatory sequence of the α2δ-4 gene; and determining the effect of the compound on the expression of the α2δ-4 protein. The term "regulatory sequence" is as defined supra.

In one embodiment, the cell-based assay comprises the step of: (1) contacting a compound with a host cell having the regulatory sequence for a α2δ-4 gene; (2) measuring the effect of the compound on the expression of the α2δ-4 protein, or the reporter; and (3) comparing the effect of the compound with that of a reference control. The host cell can be a native host cell, or a recombinant host cell. The reference control contains only the vehicle buffer to which the testing compound is dissolved. Several assay methods can be used to measure the effect of the compound on the expression of the α2δ-4 protein inside a cell. For example, gene or protein fusions comprising the regulatory sequence for a α2δ-4 and a reporter, such as green fluorescent protein (GFP) or β-galactosidase, can be used. The gene fusion is constructed such that only the transcription of the reporter gene is under control of the α2δ-4 regulatory sequence. The protein fusion is constructed so that both the transcription and translation of the reporter gene protein are under control of the α2δ-4 regulatory sequence. Preferably, a second gene or protein fusion comprising the same reporter but a different regulatory sequence (i.e., a regulatory sequence for a gene unrelated to α2δ-4 family) can be used to increase the specificity of the assay. Alternatively, a cellular phenotype attribute to α2δ-4 channel, such as a characteristic membrane potential profile, can also be used to measure the effect of the compound on the expression of the α2δ-4 protein. In addition, the effect of the compound can be assayed by measuring the amount of α2δ-4 mRNA or protein inside the cell directly using methods described supra (i.e., Northern Blot, RT-PCR, SDS-PAGE, Western Blot, etc).

In another preferred embodiment, the method involves a regulatory sequence of the α2δ-4 gene in a cell-free assay system. The cell-free assay comprises the step of: (1) contacting a compound to the regulatory sequence for a α2δ-4 gene in a cell-free assay system; (2) measuring the effect of the compound on the expression of the α2δ-4 protein; and (3) comparing the effect of the compound with that of a reference control. The reference control contains only the buffer to which the testing compound is dissolved. Examples of the cell-free assay system include the in vitro translation and/or transcription system, which are known to those skilled in the art. For example, the full length α2δ-4 cDNA, including the regulatory sequence, can be cloned on a plasmid. Then, using this construct as the template, α2δ-4 protein can be produced in an in vitro transcription and translation system. Alternatively, synthetic α2δ-4 mRNA or mRNA isolated from α2δ-4 protein producing cells can be efficiently translated in various cell-free systems, including but not limited to wheat germ extracts and reticulocyte extracts. The effect of the compound on the expression of the α2δ-4 protein can be monitored by direct measurement of the quantity of α2δ-4 mRNA or protein using methods described supra.

In another aspect the invention relates to the identification of compounds that inhibit or enhance $Ca^{2+}$ flux through a calcium channel comprising a α2δ-4 calcium channel subunit.

The invention further provides a method of identifying a compound that increases or decreases $Ca^{2+}$ flux through a calcium channel comprising a α2δ-4 calcium channel subunit. The method comprises the steps of contacting a test compound with a α2δ-4 calcium channel subunit, or a conservatively modified variant thereof, wherein said conservatively modified variant specifically binds to antibodies specifically reactive with α2δ-4 calcium channel subunit; and determining the effect of the compound to increase or decrease the flux of ions through a calcium channel comprising a α2δ-4 calcium channel subunit.

Assay methods that can be used to determine the effect of the compound to increase or decrease the flux of ions through a calcium channel are described supra.

In one embodiment, the present invention relates to a method for identifying a compound useful for increasing or decreasing expression of an α2δ-4 calcium channel subunit protein comprising the steps of contacting a test compound with a nucleic acid sequence comprising at least one regulatory sequence and a reporter gene operably linked thereto; and determining whether the test compound increases or decreases the expression of the reporter gene. In one embodiment the compound identification step is performed as a cell free assay and in another embodiment the method is performed in situ. In one embodiment the reporter gene is the α2δ-4 calcium channel subunit and in another embodiment the reporter gene is an unrelated gene. Preferably the regulatory sequence can include, but is not limited to one or more promoter sequences, one or more enhancer sequences, or a combination thereof as well as a variety of cis and trans regulatory sequences that are known in the art.

Where the method is performed in situ (i.e., in a cell based assay using intact cells), the amount of time necessary for cellular contact with the compound is empirically determined, for example, by running a time course with a known calcium channel α2δ-4 subunit modulator and measuring cellular changes as a function of time.

The term "functional" as used herein refers to the expression of a α2δ-4 protein-characteristic activity. For example, but not by way of limitation, a functional α2δ-4 calcium channel may bind gabapentin (GBP) or may act as a voltage-gated calcium channel when expressed with its calcium channel complex proteins, the alpha1, beta, and gamma subunits.

The measurement means of the method of the present invention can be further defined by comparing a cell that has been exposed to a compound to an identical cell that has not been similarly exposed to the compound. Alternatively two cells, one containing a calcium channel α2δ-4 subunit and a second cell identical to the first, but lacking a calcium channel α2δ-4 subunit can both be contacted with the same compound and compared for differences between the two cells. This technique is also useful in establishing the background noise of these assays. One of ordinary skill in the art will appreciate that these control mechanisms also allow easy selection of cellular changes that are responsive to modulation of functional calcium channel α2δ-4 subunit.

The term "cell" refers to at least one cell, but includes a plurality of cells appropriate for the sensitivity of the detection method. Cells suitable for the present invention may be bacterial, yeast, or eukaryotic.

The cellular changes contemplated within the method of the present invention comprise directly measuring changes in the function or quantity of the α2δ-4 calcium channel subunit or by measuring downstream effects of α2δ-4 calcium channel subunit function, for example by measuring secondary messenger concentrations or changes in transcription or by detecting changes in the protein levels of genes that are transcriptionally influenced by the calcium channel α2δ-4 subunit. Alternatively phenotypic changes can be measured in the cell. Preferred measurement means include changes in the quantity of calcium channel α2δ-4 subunit protein, changes in the functional activity of the calcium channel α2δ-4 subunit, changes in the quantity of mRNA, changes in intracellular protein, changes in cell surface protein, or secreted protein, or changes in $Ca^{2+}$, cAMP or GTP concentration. Changes in the quantity or functional activity of calcium channel α2δ-4 subunit are described herein. Changes in the levels of mRNA are detected by reverse transcription polymerase chain reaction (RT-PCR) or by differential gene expression. Immunoaffinity, ligand affinity, or enzymatic measurement quantitates changes in levels of protein in host cells. Protein-specific affinity beads or specific antibodies can be used to isolate labeled or unlabelled protein. Labeled protein can be visualized after separation by SDS-PAGE. Unlabelled protein can be detected by Western blotting, cell surface detection by fluorescent cell sorting, cell image analysis, ELISA or RIA employing specific antibodies. Where the protein is an enzyme, the induction of protein is monitored by cleavage of a fluorogenic or colorimetric substrate.

In another embodiment, cell membranes isolated from cells expressing the α2δ-4 subunit recombinantly or natively can be used in binding assays to determine if a compound inhibits the binding of a ligand, such as gabapentin, to the α2δ-4 subunit. The method comprising the steps of: (a) incubating a cell membrane from a cell expressing α2δ-4 subunit with a labeled ligand for α2δ-4 subunit, such as a radioactive gabapentin (GBP), and a candidate compound, wherein the membrane comprises an α2δ-4 subunit of calcium channel and where the contact is for sufficient time to allow the labeled ligand binding to the α2δ-4 subunit of calcium channels in the cell membranes; (b) separating the cell membranes from unbound labeled ligand; and (c) identifying a compound that inhibits ligand binding to the subunit by a reduction in the amount of labeled ligand binding to the cell membrane.

In yet another embodiment, substantially purified calcium channel α2δ-4 subunit protein can be used in the a binding assay, comprising: 1) contacting a compound with a measurably labeled ligand for the calcium channel α2δ-4 subunit protein, such as a radioactive gabapentin (GBP) and a calcium channel α2δ-4 subunit protein; and 2) measuring binding of the compound to the protein by a reduction in the amount of labeled ligand binding to the calcium channel α2δ-4 subunit protein.

The following examples illustrate the present invention without, however, limiting the same thereto. All patents and publications mentioned herein are incorporated entirely by reference thereto.

EXAMPLE 1

Identifying a Novel Human α₂δ Subunit

The phrase "Calcium Channel" was used as key words to search the Genbank non-redundant DNA database. Twenty-nine hits were identified as related to α₂δ subunits. Further sequence analysis led to identify two overlapping EST clones that might encode a novel human calcium channel α₂δ subunit. The accession numbers are AA001473 (572 bp in length) and H86016 (306 bp in length). The two clones were almost 100% identical in the 292 bp overlapping region, suggesting that they might encode the same polypeptide. The BLAXTX search against the Genbank non-redundant protein database revealed that the longer clone AA001473 was 40% identical to the mouse calcium channel α₂δ-3 subunit over residues 839 to 977 (Accession No. AJ10949), 36% identical to human calcium channel α₂δ-2a subunit over residues 870 to 949 (Accession No. AF042793) and 34% identical to the human calcium channel α₂δ-1 a subunit from residues 836 to 927 (Accession No. U73483), respectively.

EXAMPLE 2

Cloning of Human Voltage Gated Calcium Channel α₂δ-4 Subunit

Rapid Amplification of cDNA End (RACE-PCR)

In order to clone full-length human calcium channel α₂δ-4 subunit, three rounds of RACE-PCR were used. For the first round of RACE-PCR, two primers were synthesized based on the N-terminal sequence of EST clone AA001473. They were A2-4-9 (SEQ. ID. NO:1 5'-CAG GGG CTG GGC TGC ACT GTG GTG GTG-3') and A2-4-10 (SEQ. ID. NO:2 5'-CTC TCG GGA CCT CTT GGA GAT CAG AAT-3'). Primary Race PCR was performed in a 50 μl final volume. The reaction mixture contained 5 μl of Marathon-Ready™ human brain cDNA purchased from Clontech (Palo Alto, Calif.), 5 μl of 10× reaction buffer, 200 μM dNTP, 200 nM AP1 primer (Clontech, SEQ. ID. NO.:3 5'-CCA TCC TAA TAC GAC TCA CTA TAG GGC-3'), 200 nM human calcium channel α₂δ-4 subunit specific primer A2-4-9 and 1 μl of 50× Advatage2 DNA polymerase mixture (Clontech). The thermal cycler parameter for RACE-PCR was: initial denaturing at 94° C. for 30 sec, 5 cycles of 94° C./5 sec and 72° C./4 min, 5 cycles of 94° C./5 sec and 70° C./4 min, and 20 cycles of 94° C./5 sec and 68° C./4 min.

Nested PCR

After RACE-PCR reaction, nested PCR was performed directly to further enhance the amplification of human calcium channel α₂δ-4 subunit. The reaction mixture (in 50 μl final volume) contained: 5 μl of the above RACE PCR product, 5 μl of 10× reaction buffer, 200 μM dNTP, 200 nM AP2 primer (Clontech, SEQ. ID. NO.:4 5'-ACT CAC TAT AGG GCT CGA GCG GC-3'), 200 nM human calcium channel α₂δ-4 subunit specific primer A2-4-10 and 1 μl of 50× Advantage2 DNA polymerase mixture (Clontech). The thermal cycler parameters for the nest PCR reaction was: initial denaturing at 94° C. for 30 sec, 5 cycles of 94° C./5 sec and 72° C./4 min, 5 cycles of 94°C./5 sec and 70° C./4 min, and 20 cycles of 94° C./5 sec and 68° C./4 min.

Subcloning

The nested PCR product was then subcloned with a TA cloning kit (Invitrogen, CA). Briefly, the nest PCR product was first size fractionated on 1% agarose gel. The DNA fragments that ranged from 1 to 3 kb were excised from the gel and purified with Qiaquick Spin Purification Kit (Qiagen, CA). Six μl of purified nested PCR product was then ligated with 2 μl pCR2.1 (Invitrogen) linearized vector in the presence of 1 μl 10× reaction buffer, and 1 μl of ligase (4 U/μl) at 14° C. for 4 hours. Finally, 2 μl of ligation mixture was used and the product was used to transform bacterial TOP10F' (Invitrogen) competent cells.

Second Round RACE and Nested PCR

Sequencing analysis of the clone NQC45, a product from the first round of 5'end RACE-PCR, revealed that the α₂δ-4 cDNA had been successfully extended about 1.7 kb cDNA toward the 5'end of the cDNA. However, the N-terminal sequence information for the first 320 amino acids was still missing.

In order to clone the cDNA fragment encoding the N-terminal 320 amino acids of the human α₂δ-4 subunit, a second round of RACE-PCR was performed. Based on the N-terminal sequence of NQC45, the human calcium channel α₂δ-4 subunit specific primer A2-4-16 (SEQ. ID. NO.:5 5'-CAG GCT CTG AGC CTG CGA GCT GAG-3') and A2-4-17 (SEQ. ID. NO.:6 5'-ATG TCG TGG TCG TGG TTG ATG ACC AT-3') were synthesized. The second RACE-PCR was performed with A2-4-16 and AP1 primers and followed nested PCR using A2-4-17 and AP2 primers under condition used in the 1ˢᵗ round of RACE and nested PCR. The nested PCR product was then size fractionated on a 1% agarose gel and a DNA fragment about 1 kb was excised, purified and subcloned into a pCR2.1 cloning vector, as described previously.

Sequence analysis of the clones revealed that the second round of RACE-PCR extended the cDNA fragment through to 190 bp of the 5' untranslational region. An in-frame stop codon (TGA) is present 30 bp upstream from the first methinione. The adjacent upstream sequence (CAGGCC ATGG, especially at −3 position G and +4 position G) of the first ATG is similar to a Kozak sequence (5'-GCCA/GCC AUGG-3'), suggesting a site for translational initiation (Kozak, (1991) *J. Cell. Biol.* 115:887–903). Therefore, the translational open reading frame may start at the ATG codon located at position 190. Starting from this ATG codon, the open reading frame contains 3273 bp encoding a polypeptide of 1090 amino acids (SEQ ID NO:10) and having a calculated molecular mass of 123.2 kDa. The deduced primary sequence is shown in SEQ ID NO:9. Protein sequence analysis revealed that the human calcium channel α₂δ-4 subunit containing multiple N-glycosylational sites are located at residues 94, 137, 455, 600, 682 and 1013, respectively. The human α₂δ-4 subunit also contains two putative PKA (protein kinase A) sites (at residues 60 and 633), and 14 PKC sites (protein kinase C).

5. Assembly of Full-Length Human Calcium Channel α₂δ-4 Subunit:

The full-length human calcium channel α₂δ-4 subunit was assembled and subcloned into pAGA3 vectors as described in Qin et al. (1997), supra, according to standard molecular biology methods. Briefly, the 1.26 kb N-terminal fragment from 190 bp (NcoI site with start codon) to 1452 bp (KpnI which was derived from the pCR2.1 vector) was cloned into the pAGA3 vector. The resulting construct was designated pAGA3/hα₂δ4-NT. The three C-terminal fragments were subcloned into pBS (KS) (Stratagene) by two steps. First, the two 0.9 kb fragments from 1639 bp (HindIII) to 2575 bp (EcoRI) and 2575 (EcoRI) to the end (BglII, derived from vector) were subcloned together with pBS digested with HindIII and BamHI. Then, a 0.3 kb fragment from 1350 bp (SalI, derived from vector) to 1639 bp (HindIII) was subcloned into the construct obtained from the first step following XhoI and HindIII digestion and ligation producing the construct pBS/hα₂δ4-CT. Finally, the 2.1 kb DNA fragment excised from pBS/hα₂δ4-CT by digestion with BglII and XbaI was subcloned into pAGA3/hα₂δ4-NT digested with the same restriction enzymes to generate the full-length human calcium channel α₂δ-4 subunit, pAGA3/hα₂δ-4. The final construct was confirmed by DNA sequencing.

The deduced amino acid sequence (SEQ ID NO.:9) along with the nucleic acid sequence (SEQ ID NO.:10) encoding the human calcium channel α₂δ-4 subunit is provided below:

```
CAGCTACATTCAGCAGAGCCCAAGTCTGCCACTCTCCAACCaGAGGCCCTGGAAGCTTGG                                                60

GGTCAAGCTCAGTCCTGGGCTCGTCAGCCCGGCCCCACAACCCTCAGCAGGAGaACCTGC                                                120

CGAGGACATTCAGCACACAGCAGTGCAGCCGCTGGGTCCTGAGGGTTCTCCGCGTCTCCT                                                180

GCCCAGGCCATGGCTGTAGCTTTAGGGACAAGGAGGAGGGACAGAGTGAAGCTATGGGCT                                                240
         MetAlaValAlaLeuGlyThrArgArgArgAspArgValLysLeuTrpAla                                                  —

GACACCTTCGGCGGGGACCTGTATAACACTGTGACCAAATACTCAGGCTCTCTCTTGCTG                                                300
AspThrPheGlyGlyAspLeuTyrAsnThrValThrLysTyrSerGlySerLeuLeuLeu                                                  —

CAgAAGAAGTACAACGATGTGGAGTCCAGTCTGAAGATCGAGGAGGTGGATGGCTTGGAG                                                360
GlnLysLysTyrLysAspValGluSerSerLeuLysIleGluGluValAspGlyLeuGlu                                                  —

CTGGTGAGGAAGTTCTCAGAGGACATGGAGAACATGCTGCGGAGGAAAGTCgAGGCGGTC                                                420
LeuValArgLysPheSerGluAspMetGluAsnMetLeuArgArgLysValGluAlaVal                                                  —

CAgAATCTGGTGGAAGCTGCCCAGGAGGCCGACCTGAACCACGAATTCAATGAATCCCTG                                                480
GlnAsnLeuValGluAlaAlaGlnGluAlaAspLeuAsnHisGluPheAsnGluSerLeu                                                  —

GTGTTCGACTATTACAACTCGGTCCTGATCAACGaGAGGGACGAGAAGGGCaACTTcGTG                                                540
ValPheAspTyrTyrAsnSerValLeuIleAsnGluArgAspGluLysGlyAsnPheVal                                                  —

GAGCTGGGCGCCGAGTTCCTCCTGGAGTCCAATGCTCaCTTCAGCAACCTGCCGGtGAAC                                                600
GluLeuGlyAlaGluPheLeuLeuGluSerAsnAlaHisPheSerAsnLeuProValAsn                                                  —

ACCTCCATCAGCAGCGTGCAGCTGCCCACCAACGTGTACAACAAAGACCCAGATATTTTA                                                660
ThrSerIleSerSerValGlnLeuProThrAsnValTyrAsnLysAspProAspIleLeu                                                  —

AATGGAGTCTACATGTCTGAAgCCTTGAATGCTGTCTTCGTGGAGAACTTCCAGAGAGAC                                                720
AsnGlyValTyrMetSerGluAlaLeuAsnAlaValPheValGluAsnPheGlnArgAsp                                                  —

CCAACGTTGACCTGGCAATATTTTGGCAGTGCAACTGGATTCTTCAGGAtCTATCCAGGT                                                780
ProThrLeuThrTrpGlnTyrPheGlySerAlaThrGlyPhePheArgIleTyrProGly                                                  —

ATAAAATGGACACCTGaTGAGAATGGAGTCATTACTTTTGACTGCCGAAACCGCGGCTGG                                                840
IleLysTrpThrProAspGluAsnGlyValIleThrPheAspCysArgAsnArgGlyTrp                                                  —

TACATTCAAGCTGCTACTTCTCCCAAGGACATAGTGATTTTGGTGGACGTGAGCGGCAGT                                                900
TyrIleGlnAlaAlaThrSerProLysAspIleValIleLeuValAspValSerGlySer                                                  —

ATGAAGGGGCTGAGGATGACTATTGCCaAGCACaCCATCACCACCATCTTGGACACCCTG                                                960
MetLysGlyLeuArgMetThrIleAlaLysHisThrIleThrThrIleLeuAspThrLeu                                                  —

GGGGAGAATGACtTCGTTAATATCATAGCGTACAATGACTACGTCCATTACATCGAGCCT                                                1020
GlyGluAsnAspPheValAsnIleIleAlaTyrAsnAspTyrValHisTyrIleGluPro                                                  —

TGTTTTAAAGGGATCCTCGTCCaGGCGGACCGAGACAATCGAGAGCATTTCAAACTgCTG                                                1080
CysPheLysGlyIleLeuValGlnAlaAspArqAspAsnArgGluHisPheLysLeuLeu                                                  —

GTGGAGGAGTTGATGGTCAAAgGTGTGGGGGTCGTGGACCAAGCCCTGAGAGAAGCCTTC                                                1140
ValGluGluLeuMetValLysGlyValGlyValValAspGlnAlaLeuArgGluAlaPhe                                                  —

CAGATCCTGAAgCAGTTCCAAGAgGCCAAGCAAGGAAGCCTCTGCAACCAGGCCATCATG                                                1200
GlnIleLeuLysGlnPheGlnGluAlaLysGluGlySerLeuCysAsnGlnAlaIleMet                                                  —

CTCATCAgCGACgGCGCCGTGGAGGACTACGAGCCGGTGTTTGAGAAGTATAACTGGCCA                                                1260
LeuIleSerAspGlyAlaValGluAspTyrGluProValPheGluLysTyrAsnTrpPro                                                  —

GACTGTAAGGTCCGAGTTTTCACTTACCTCATTGGGAGAGAAGTGTCTTTTGCTGACCGC                                                1320
AspCysLysValArgValPheThrTyrLeuIleGlyArgGluValSerPheAlaAspArg                                                  —

ATGAAGTGGATTGCATGCAACAACAAAGGctACTACACGCAGATCTCAACGCTGGCGGAC                                                1380
MetLysTrpIleAlaCysAsnAsnLysGlyTyrTyrThrGlnIleSerThrLeuAlaAsp                                                  —

ACCCAGGAGAACGTGATGGAATACCTGCACGTCCTCAGCCGCCCCATGGTCATCAACCAC                                                1440
ThrGlnGluAsnValMetGluTyrLeuHisValLeuSerArgProMetValIleAsnHis                                                  —

GACCACGACATCATCTGCACAGAGGCCTACATGGACAGCAACCTCCTCAGCTCGCAGGCT                                                1500
AspHisAspIleIleTrpThrGluAlaTyrMetAspSerLysLeuLeuSerSerGlnAla                                                  —

CAGAGCCTGACACTGCTCACCACTGTGGCCATGCCAGTCTTCAGCAAGAAGAACGAAACG                                                1560
GlnSerLeuThrLeuLeuThrThrValAlaMetProValPheSerLysLysAsnGluThr                                                  —

CGATCCCATGGCATTCTCCTGGGTGTGGTGGGCTCAGATGTGGCCCTGAGAGAGCTGATG                                                1620
ArgSerHisGlyIleLeuLeuGlyValValGlySerAspValAlaLeuArgGluLeuMet                                                  —

AAGCTGGCGCCCCGGTACAAGCTTGGAGTGCACGGATACGCCTTTCTGAACACCAACAAT                                                1680
LysLeuAlaProArgTyrLysLeuGlyValHisGlyTyrAlaPheLeuAsnThrAsnAsn                                                  —
```

-continued

| | |
|---|---|
| GGCTACATCCTCTCCCATCCCOACCTCCGGCCCCTGTACAGAGAGGGGAAGAAACTAAAA<br>GlyTyrIleLeuSerHisProAspLeuArgProLeuTyrArgGluGlyLysLysLeuLys | 1740 |
| CCCAAACCTAACTACAACAGTGTGGATCTCTCCGAAGTGGAGTGGGAAGACCAGGCTGAA<br>ProLysProAsnTyrAsnSerValAspLeuSerGluValGluTrpGluAspGlnAlaGlu | 1800 |
| TCTCTGAGAACAGCCATGATCAATAGGGAAACAGGTACTCTCTCGATGGATGTGAAGGTT<br>SerLeuArgThrAlaMetIleAsnArgGluThrGlyThrLeuSerMetAspValLysVal | 1860 |
| CCGATGGATAAAGGGAAGCGAGTTCTTTTCCTGACCAATGACTACTTCTTCACGGACATC<br>ProMetAspLysGlyLysArgValLeuPheLeuThrAsnAspTyrPhePheThrAspIle | 1920 |
| AGCGACACCCCTTTCAGTTTGGGGCGGTGCTGTCCCGGGGCCACGGAGAATACATCCTT<br>SerAspThrProPheSerLeuGlyAlaValLeuSerArgGlyHisGlyGluTyrIleLeu | 1980 |
| CTGGGGAACACGTCTGTGGAAGAAGGCCTGCATGACTTGCTTCACCCAGACCTGGCCCTG<br>LeuGlyAsnThrSerValGluGluGlyLeuHisAspLeuLeuHisProAspLeuAlaLeu | 2040 |
| GCCGGTGACTGGATCTACTGCATCACAGATATTGACCCAGACCACCGGAAGCTCAGCCAG<br>AlaGlyAspTrpIleTyrCysIleThrAspIleAspProAspHisArgLysLeuSerGln | 2100 |
| CTAGAGGCCATGATCCGCTTCCTCACCAGGAAGGACCCAGACCTGGAGTGTGACGAGGAG<br>LeuGluAlaMetIleArgPheLeuThrArgLysAspProAspLeuGluCysAspGluGlu | 2160 |
| CTGGTCCGGGAGGTGCTGTTTGACGCGGTGGTGACAGCCCCCATGGAAGCCTACTGGACA<br>LeuValArgGluValLeuPheAspAlaValValThrAlaProMetGluAlaTyrTrpThr | 2220 |
| GCGCTGGCCCTCAACATGTCCGAGGAGTCTGAACACGTGGTGGACATGGCCTTCCTGGGC<br>AlaLeuAlaLeuAsnMetSerGluGluSerGluHisValValAspMetAlaPheLeuGly | 2280 |
| ACCCGGGCTGGCCTCCTGAGAAGCAGCTTGTTCGTGGGCTCCGAGAAGGTCTCCGACAGG<br>ThrArgAlaGlyLeuLeuArgSerSerLeuPheValGlySerGluLysValSerAspArg | 2340 |
| AAGTTCCTGACACCTGAGGACGAGGCCAGCGTGTTCACCCTGGACCGCTTCCCGCTGTGG<br>LysPheLeuThrProGluAspGluAlaSerValPheThrLeuAspArgPheProLeuTrp | 2400 |
| TACCGCCAGGCCTCAGAGCATCCTGCTGGCAGCTTCGTCTTCAACCTCCGCTGGGCAGAA<br>TyrArgGlnAlaSerGluHisProAlaGlySerPheValPheAsnLeuArgTrpAlaGlu | 2460 |
| GGACCAGAAAGTGCGGGTGAACCCATGGTGGTGACGGCAAGCACAGCTGTGGCGGTGACC<br>GlyProGluSerAlaGlyGluProMetValValThrAlaSerThrAlaValAlaValThr | 2520 |
| GTGGACAAGAGGACAGCCATTGCTGCAGCCGCGGGCGTCCAAATGAAGCTGGAATTCCTC<br>ValAspLysArgThrAlaIleAlaAlaAlaAlaGlyValGlnMetLysLeuGluPheLeu | 2580 |
| CAGCGCAAATTCTGGGCGGCAACGCGGCAGTGCAGCACTGTGGATGGGCCGTACACACAG<br>GlnArgLysPheTrpAlaAlaThrArgGlnCysSerThrValAspGlyProTyrThrGlu | 2640 |
| AGCTGCGAGGACAGTGATCTGGACTGCTTCGTCATCGACAACAACGGGTTCATTCTGATC<br>SerCysGluAspSerAspLeuAspCysPheValIleAspAsnAsnGlyPheIleLeuIle | 2700 |
| TCCAAGAGGTCCCGAGAGACGGGAAGATTTCTGGGGGAGGT99aTGGTGCTGTCCTGACC<br>SerLysArgSerArgGluThrGlyArgPheLeuGlyGluValAspGlyAlaValLeuThr | 2760 |
| CAGCTGCTCAGCATGGGGGTGTTCAGCCAAGTGACTATGTATGACTATCAGGCCATGTGC<br>GlnLeuLeuSerMetGlyValPheSerGlnValThrMetTyrAspTyrGlnAlaMetCys | 2820 |
| AAACCCTCGAGTCACCACCACAGTGCAGCCCAGCCCCTGGTCAGCCCAATTTCTGCCTTC<br>LysProSerSerHisHisHisSerAlaAlaGlnProLeuValSerProIleSerAlaPhe | 2880 |
| TTGACGGCGACCAGGTGGCTGCTGCAGGAGCTGGTGCTGTTCCTGCTGGAGTGGAGTGTC<br>LeuThrAlaThrArgTrpLeuLeuGlnGluLeuValLeuPheLeuLeuGluTrpSerVal | 2940 |
| TGGGGCTCCTGGTACGACAGAGGGGCcgaGGCCAAAAGTGTCTTCCATCACTCCCACAAA<br>TrpGlySerTrpTyrAspArgGlyAlaGluAlaLysSerValPheHisHisSerHisLys | 3000 |
| CACAagaagCAGGACCCGCTGCagCCCTGCgaCaCGgagtACCCCgTGTtCGTGTACCaG<br>HisLysLysGlnAspProLeuGlnProCysAspThrGluTyrProValPheValTyrGln | 3060 |
| CCGGccaTCCGGGaggCCAACGGGATCGTGGAGTGCGGGCCCTGCCAGAAGGTATTTGTG<br>ProAlaIleArgGluAlaAsnGlyIleValGluCysGlyProCysGlnLysValPheVal | 3120 |
| GTGCAGCAGATTCCCAACAGTAACCTCCTCCTCCTGGTGACAGACCCCACCTGTGACTGC<br>ValGinGinIleProAsnSerAsnLeuLeuLeuLeuValThrAspProThrCysAspCys | 3180 |
| AGCATCTTCCCACCAGTGCTGCAGGAGGCGACAGAAGTCAAATATAATGCCTCTGTCAAA<br>SerIlePheProProValLeuGlnGluAlaThrGluValLysTyrAsnAlaSerValLys | 3240 |
| TGTGACCGGATGCGCTCCCAGaagctccGCCGGCGACCAGACTCCTGCCACGCCTTCCAT | 3300 |

-continued

```
CysAspArgMetArgSerGlnLysLeuArgArgArgProAspSerCysHisAlaPheHis

CCAGAGGTGCGGGTTGAGGCGGATCGAGGGTGGGCTGGATTTTCATCCCCAAACCCTCTG         3360
ProGluValArgValGluAlaAspArgGlyTrpAlaGlyPheSerSerProAsnProLeu

TGCCTGGGTCTGTGCCCCTGCAGACAGGAGCATATAGGGATGCCAATGAACACACCTGTG         3420
CysLeuGlyLeuCysProCysArgGlnGluHisIleGlyMetProMetAsnThrProVal

CCTGTGCTTCTCGGGGGAAACATTCGCGTTTATGCCCTGTGACACTGTGATATAATAAGA         3480
ProValLeuLeuGlyGlyAsnIleArgValTyrAlaLeuEnd

AACAGA                                                                3486
```

Sequence comparison of the human calcium channel $\alpha_2\delta$-4 subunit with the other human calcium channel $\alpha_2\delta$ subunits demonstrated that the amino acid sequence of human calcium channel $\alpha_2\delta$-4 subunit (SEQ ID NO: 10) is 30%, 32%, 61%, and 96% identical to human calcium channel $\alpha_2\delta$-1, $\alpha_2\delta$-2, $\alpha_2\delta$-3, and $\alpha_2\delta$-D subunits, respectively.

EXAMPLE 3

Genomic Structure and Splicing Variants of Human Calcium Channel $\alpha_2\delta$-4 Subunit The full-length cDNA sequence of the human calcium channel $\alpha_2\delta$-4 subunit was used to search the Genbank human genome database. The search indicated that the gene encoding the human $\alpha_2\delta$-4 subunit is localized at chromosome 12p13.3, about 400 kb away from the locus of human L-type calcium channel $\alpha_1 1.2$ ($\alpha_{1C}$) subunit (Ertel, et al., (2000) *Neuron* 25:533–535). The gene spans about 130 kb of human genome.

As shown in FIG. 1, the human calcium channel α2δ-4 cDNA is composed of 38 exons. Although the nucleotide sequence from exon 2 to exon 36 (nt 225 to 3308 of SEQ ID NO: 9) is identical to the corresponding portion of the human calcium channel $\alpha_2\delta$-D cDNA, the 5'-end exon 1 (nt 1 to 224 of SEQ ID NO:9 ) and 3'-end exon 37(nt 3308 to 3486 of SEQ ID NO:9) are clearly unique to the the α2δ-4 cDNA. To differentiate from the $\alpha_2\delta$-4 cDNA, the 5'- and 3'-ends of $\alpha_2\delta$-D are named herein as exon 1B and exon 37B, respectively. No sequence homology is observed between exon 1 and 1B, or exon 37 and 37B, indicating that both α2δ-4 and $\alpha_2\delta$-D are derived from the same gene α2δ-4 and are generated by differential splicing.

Both exon 1 and 1B have an in-frame start codon and both exon 37 and 37B have an in-frame stop codon, suggesting that there are four possible types of alternative splicing variants: (1) exon 1, 2–36, and 37; (2) exon 1B, 2–36, and 37; (3) exon 1, 2–36, and 37B; and (4) exon 1B, 2–36, and 37B. The $\alpha_2\delta$-D subunit is encoded by the fourth splicing variant. It is intended that the "α2δ-4 subunit" as used herein is encoded by only the other three splicing variants comprising either exon 1, and/or exon 37.

EXAMPLE 4

Generation of Polyclonal Antibodies

Two oligopeptides derived from both the middle and carboxyl termini of the human calcium channel $\alpha_2\delta$-4 subunit were designed in order to raise polyclonal antibodies in rabbits. The amino acid sequences for the two oligopeptides were:

(1) Ac-KVSDRKFLTPEDEASVC-amide (SEQ ID NO.:7), which includes amino acids 713 to 729 of SEQ ID NO:10, and (2) (2) Ac-RVEADRGWAGFSSPNPLC-amide (SEQ ID NO.:8), which includes amino acids 1041 to 1057 of SEQ ID NO:10.

The oligopeptides were synthesized and antibodies were to these oligopeptides were raised and purified by BioSource International, Inc. The resulting antibodies were tested by ELISA against the antigen oligopeptides and affinity purified with the same peptides. Serum and affinity purified antibodies were used for immunoanalysis, including as Western blot, immunoprecipitation, immunocytochemistry and immunohistochemistry.

EXAMPLE 5

In Vitro Translation Analysis of Human Calcium Channel $\alpha_2\delta$-4 Subunit The full-length cDNA of human calcium channel $\alpha_2\delta$-4 subunit was first subcloned into a pAGA3 vector, which was engineered for high high efficiency of in vitro transcription and translation as described in Qin et al. (1997), supra. The subcloning procedure used was described in Example 2 and produced the full-length human calcium channel $\alpha_2\delta$-4 subunit. In vitro translation of the human calcium channel $\alpha_2\delta$-4 subunit was done with TnT® T7 Quick Coupled Transcription/Translation System (Promega) following the vendor recommended protocol. Briefly, 1 μg h$\alpha_2\delta$-4/pAGA3 construct was added to 40 μl of TNT Quick Master Mix with 2 μl of [$^{35}$S]methionine (1000 Ci/mmmol at 10 mCi/ml) in a final volume of 50 μl. The reaction mixture was incubated at 30° C. for 90 min. Two μl of reaction mixture was mixed with an equal volume of SDS/PAGE loading buffer and subjected to 8–16% SDS/PAGE analysis. After electrophoresis, the gel was stained with Commassie Blue R250, dried and exposed to X-ray film. The in vitro translated human calcium channel $\alpha_2\delta$-4 subunit migrated to the molecular weight of 123 kDa as predicted by translation of the amino acid sequences from the corresponding nucleic acid sequences.

The in vitro translated human calcium channel $\alpha_2\delta$-4 subunit was also analyzed by Western blot. Briefly, 1 ml of in vitro translated human calcium channel $\alpha_2\delta$-4 subunit was subjected to 8–16% SDS PAGE. The protein on the gel was then transferred to nitrocellulose. The blot was blocked with 5% dry milk in TTBS (0.5% Tween 20, 100 mM Tris-HCl, pH7.5, 0.9% NaCl) at room temperature for 1 hour and then incubated with affinity purified anti-human $\alpha_2\delta$-4 polyclonal antibodies (1:1000 dilution with fresh block solution) at 4° C. overnight. The next day the blot was washed three times with 100 ml TTBS, and incubated with goat anti-rabbit IgG antibody conjugated with Horseradish Peroxidase (Pierce) at room temperature for 1 hour. After washed three times with 100 ml TTBS, the blot was visualized with luminescent reagents, ECL-Plus (Amersham-Pharmacia Biotech).

EXAMPLE 6

Northern Blot Analysis of the Human Calcium Channel $\alpha_2\delta$-4 Subunit Expression Northern blot analysis was used to assess tissue distribution of the human calcium channel $\alpha_2\delta$-4 subunit. The cDNA fragment encoding residues 1–270 of human calcium channel α$_2$δ-4 subunit was used as probe. To make the probe, a 710 bp DNA fragment was isolated and purified from pAGA3/hα$_2$δ4-NT by digesting with NcoI and EcoRI. To label the probe, 25 ng of a DNA fragment encoding 1–270 residues of the human calcium channel α$_2$δ-4 subunit was denatured in final volume of 45 μl at 99° C. for 4 min. The denatured DNA probe was incubated with 5 μl of [α$^{32}$P]dCTP at 6000 Ci/mmol (Amersham Pharmacia Biotech) and then transferred to the tube containing a READY-TO-GO DNA Labeling Bead (-dCTP) (Amersham Pharmacia Biotech) and incubated at 37° C. for 30 min. The labeled probe was then separated from free [α$^{32}$P]dCTP with MICROSPIN G-50 column (Amersham Pharmacia Biotech). The labeled probe was denatured by incubating at 99° C. for 4 min and immediately placed on ice before being added to the hybridization solution.

Human MTN (Multiple Tissue Northern) blot (Cal. No.7760-1) was purchased from Clontech (Palo Alto, Calif.) and included samples from heart, brain, placenta, lung, liver, skeletal muscle, kidney, and pancreas. The blots were pre-hybridized with 5 ml ExpressHyb Solution (Clontech) at 65° C. for 4 hours, and then hybridized in the presence of 2×10$^6$ cpm/μl probe of the human α2δ-4 subunit at 65° C. for overnight. The probe was a [$^{32}$P]-labeled 270 bp cDNA fragment encoding 90 amino terminal residues of the human calcium channel α$_2$δ-4 subunit. The blots were washed twice with 200 ml of 0.2×SSC/0.1% SDS solution at 65° C. for two hours. Finally the blots were exposed to X-ray film in a −80° C. freezer for 1–3 days.

A 2.0 kb cDNA fragment encoding human β-actin was used as a control probe. The same blots were striped with 0.5% SDS at 90° C. for 10 min after hybridization with the human calcium channel α$_2$δ-4 probe. The blots were then prehybridized with 5 ml of ExpressHyb at 68° C. for 1 hour and then hybridized in the presence of a human β-actin probe for 2 hours at 68° C. The blots were washed twice with 200 ml of 0.2×SSC/0.1% SDS solution at 68° C. for two hours. Finally the blots were exposed to X-ray film in −80° C. freezer for 6 hours. In these studies, the VGCC containing α$_2$δ-4 appeared most strongly in heart and skeletal muscle.

EXAMPLE 7

Cloning of Human Calcium Channel α$_2$δ-4 Subunit cDNA into a Mammalian Expression Vector The human calcium channel α$_2$δ-4 subunit gene was inserted into pcDNA3.1 (Invitrogen) by a three piece ligation. The 850 bp cDNA fragment encoding the amino terminal portion of the human calcium channel α$_2$δ-4 subunit was obtained from pAGA3/hα$_2$δ-4-NT by digesting with NcoI, followed by blunt end digestion with BamHI. The 2.6 kb cDNA fragment encoding the carboxyl terminal portion of the human calcium channel α$_2$δ-4 subunit was isolated and purified from pAGA3/hα$_2$δ-4 by digestion with BamHI and XbaI. The two cDNA fragments were ligated together with the vector pcDNA3, previously digested with EcoRV and XbaI. The recombinant plasmids containing the human calcium channel α$_2$δ-4 subunit were isolated and confirmed by restriction enzyme digestion and DNA sequencing.

The clone pcDNA3.1/hα$_2$δ-4 was used for transient and stable transfection of HEK293 cells by SuperFect (Qiagen) following the vendor's protocol. Stable cell clones were selected for growth in the presence of G418. Single G418 resistant clones were isolated and shown to contain the intact human calcium channel α$_2$δ-4 subunit cDNA. Clones containing the human calcium channel α$_2$δ-4 subunit cDNAs were analyzed for expression using immunological techniques, such as Western blot, immunoprecipitation, and immunofluorescence using antibodies specific to the human calcium channel α$_2$δ-4 subunit. The binding affinity of the human calcium channel α$_2$δ-4 subunit to Gabapentin was determined by radioactive ligand binding assay.

Cells that were expressing the human calcium channel α$_2$δ-4 subunit, stably or transiently, were used to test for channel protein expression and for ligand binding activity. These cells were used to identify and examine other compounds for their ability to modulate, inhibit or activate the channel and to compete for radioactive ligand binding.

Cassettes containing the human calcium channel α$_2$δ-4 subunit cDNA in the positive orientation, with respect to the promoter, were ligated into appropriate restriction sites 3' of the promoter and identified by restriction site mapping and/or sequencing. These cDNA expression vectors were introduced into fibroblast host cells such as COS-7 (ATCC# CRL1651), and CV-1 tat (Sackevitz et al., Science 238: 1575 (1987), or 293, L (ATCC# CRL6362) by standard methods including, but not limited to, electroporation, or chemical procedures (such as cationic liposomes, DEAE dextran, or calcium phosphate). Transfected cells and cell culture supernatants were harvested and analyzed for human calcium channel α$_2$δ-4 subunit expression as described herein.

The vectors used for mammalian transient expression are be used to establish stable cell lines expressing the human calcium channel α$_2$δ-4 subunit. The human calcium channel α$_2$δ-4 subunit is expressed extracellularly as a secreted protein by ligating human calcium channel α$_2$δ-4 subunit cDNA constructs to DNA encoding the signal sequence of a secreted protein, as known in the art. The transfection host cells include, but are not limited to, CV-1-P (Sackevitz et al., Science 238: 1575 (1987), tk-L (Wigler, et al. Cell 11: 223 (1977), NS/0, and dHFr-CHO (Kaufman and Sharp, J. Mol. Biol. 159: 601, (1982).

Co-transfection of any vector containing human calcium channel α$_2$δ-4 subunit cDNA with a drug selection plasmid including, but not limited to, G418, aminoglycoside phosphotransferase; hygromycin, hygromycin-B phosphotransferase; APRT, or xanthine-guanine phosphoribosyl-transferase will allow for the selection of stably transfected clones. Levels of Human α2δ-4 calcium channel subunit are quantitated by the assays described herein.

Human calcium channel α$_2$δ-4 subunit cDNA constructs are also ligated into vectors containing amplifiable drug-resistance markers for the production of mammalian cell clones synthesizing the highest possible levels of human calcium channel α$_2$δ-4 subunit. Following introduction of these constructs into cells, clones containing the plasmid are selected with the appropriate agent. Isolation of an over-expressing clone with a high copy number of plasmids, is accomplished by selection in increasing doses of the agent.

The expression of recombinant human calcium channel α$_2$δ-4 subunit is achieved by transfection of full-length human calcium channel α$_2$δ-4 subunit cDNA into a mammalian host cell.

EXAMPLE 8

Cloning of Human Calcium Channel α$_2$δ-4 Subunit cDNA into a Baculovirus Expression Vector for Expression in Insect Cells Baculovirus vectors, which are derived from the genome of the AcNPV virus, are designed to provide high level expression of cDNA in the Sf9 line of insect cells (ATCC CRL# 1711). Recombinant baculoviruses expressing Human $\alpha_2\delta$-4 subunit cDNA is produced by the following standard methods (InVitrogen Maxbac Manual): the Human calcium channel $\alpha_2\delta$-4 subunit cDNA constructs are ligated into the polyhedrin gene in a variety of baculovirus transfer vectors, including the pAC360 and the BlueBac vector (InVitrogen). Recombinant baculoviruses are generated by homologous recombination following co-transfection of the baculovirus transfer vector and linearized AcNPV genomic DNA [Kitts, P. A., *Nucl. Acid. Res.* 18: 5667 (1990)] into Sf9 cells. Recombinant pAC360 viruses are identified by the absence of inclusion bodies in infected cells and recombinant pBlueBac viruses are identified on the basis of β-galactosidase expression. Following plaque purification, human calcium channel $\alpha_2\delta$-4 subunit expression is measured by the assays described herein.

The cDNA encoding the entire open reading frame for human calcium channel $\alpha_2\delta$-4 subunit is inserted into pBlue-Bacil. Constructs in the positive orientation are identified by sequence analysis and used to transfect Sf9 cells in the presence of linear AcNPV mild type DNA.

Authentic, active human calcium channel $\alpha_2\delta$-4 subunit is found in the cytoplasm membrane of infected cells. Active human calcium channel $\alpha_2\delta$-4 subunit is extracted from infected cells by methods known in the art (including, for example, hypotonic or detergent lysis).

EXAMPLE 9

Cloning of Human Calcium Channel $\alpha_2\delta$-4 Subunit cDNA into a Yeast Expression Vector Recombinant human calcium channel $\alpha_2\delta$-4 subunit is produced in the yeast *S. cerevisiae* following the insertion of the optimal human calcium channel $\alpha_2\delta$-4 subunit cDNA cistron into expression vectors designed to direct the intracellular or extracellular expression of heterologous proteins. In the case of intracellular expression, vectors such as EmBLyex4, or the like, are ligated to the human calcium channel $\alpha_2\delta$-4 subunit cistron (see Rinas, U. et al., *Biotechnology* 8: 543–545 (1990); and Horowitz B. et al., *J. Biol. Chem.* 265: 4189–4192 (1989). For extracellular expression, the human calcium channel $\alpha_2\delta$-4 subunit cistron is ligated into yeast expression vectors which fuse a secretion signal (a yeast or mammalian peptide) to the NH$_2$ terminus of the Human calcium channel $\alpha_2\delta$-4 subunit protein (Jacobson, M. A., *Gene* 85: 511–516 (1989) and Rieft L. and Bellon N. *Biochem.* 28: 2941–2949 (1989).

These vectors include, but are not limited to, pAVE1.6, which fuses the human serum albumin signal to the expressed cDNA (Steep O. *Biotechnology* 8: 42–46 (1990), and the vector pL8PL which fuses the human lysozyme signal to the expressed cDNA (Yamamoto, Y., *Biochem.* 28: 2728–2732). In addition, the human calcium channel $\alpha_2\delta$-4 subunit is expressed in yeast as a fusion protein conjugated to ubiquitin using the vector pVEP (see Ecker, D. J., *J. Biol. Chem.* 264: 7715–7719 (1989), Sabin, E. A., *Biotechnology* 7: 705–709 (1989), and McDonnell D. P., *Mol. Cell Biol.* 9: 5517–5523 (1989). The levels of expressed human calcium channel $\alpha_2\delta$-4 subunit are determined by the assays described herein.

EXAMPLE 10

Purification of Recombinant Human Calcium Channel $\alpha_2\delta$-4 Subunit

Recombinantly produced human calcium channel $\alpha_2\delta$-4 subunit may be purified by antibody affinity chromatography.

Human calcium channel $\alpha_2\delta$-4 subunit antibody affinity columns are made by adding the anti-human calcium channel $\alpha_2\delta$-4 subunit antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) together with appropriate membrane solubilizing agents such as detergents. The cell culture supernatants or cell extracts containing solubilized human calcium channel $\alpha_2\delta$-4 subunit are slowly passed through the column. The column is then washed with phosphate-buffered saline together with detergents until the optical density ($A_{280}$) falls to background, then the protein is eluted with 0.23 M glycine-HCl (pH 2.6) together with detergents. The purified human calcium channel $\alpha_2\delta$-4 subunit protein is then dialyzed against phosphate buffered saline.

EXAMPLE 11

Immunohistochemistry

Commercial human checkerboard tissue slides (Dako, Carpenteria, Calif.; Biomeda, Foster City, Calif.; Novagen, Milwaukee, Wis.) were deparaffinized, hydrated and processed for routine immunohistochemistry (IHC) as previously described (D'Andrea et al., (1998) *J. Histochem. Cytochem.* 46(1): 1–8. Briefly, slides were microwaved in Target buffer (Dako), cooled, placed in distilled H$_2$O and then treated with 3.0% H$_2$O$_2$ for 10 min. Afterwards, the slides were rinsed in phosphate-buffered saline (pH 7.4, PBS) and then processed through an avidin-biotin blocking system according to the manufacturer's instructions (Vector Labs, Burlingame, Calif.) and then placed in PBS. All subsequent reagent incubations and washes were performed at room temperature. Normal blocking serum (Vector Labs) was placed on all slides for 10 min. After briefly rinsing in PBS, primary antibody (affinity purified anti-human $\alpha_2\delta$-4 polyclonal antibodies, 1:1000 dilution) was placed on slides for 30 min. The slides were washed and biotinylated secondary antibody, here goat anti-rabbit (polyclonal antibodies) or horse anti-mouse (monoclonal antibodies) were placed on the tissue sections for 30 min (Vector Labs). After rinsing in PBS, the avidin-horseradish peroxidase-biotin complex reagent (HRP-ABC, Vector Labs) was added for 30 min. Slides were washed and treated with the chromogen 3,3'-diaminobenzidine (DAB, Biomeda) twice for five min each, then rinsed in dH$_2$O, and counterstained with hematoxylin. A monoclonal antibody to vimentin, the widely conserved ubiquitous, intracellular filament protein, was utilized as a positive control to demonstrate tissue antigenicity and control reagent quality. The negative controls included replacement of the primary antibody with pre-immune serum or with the same species IgG isotype non-immune serum.

The results are summarized in Table 1

TABLE 1

Tissue distribution of human calcium channel $\alpha_2\delta$-4 subunit determined by immunohistochemistry

| Tissue | Cell type | Protein level |
|---|---|---|
| Adrenal | Medulla | +/++ |
| Pituitary | Basophiles | +++ |
|  | other cell types | − |
| Brain | Neurons | +/+/− |
|  | Astrocytes | − |
|  | Purkinje cells | ++/+ |
|  | Fibers | +/− |
| Breast | Epithelium | +/− |
|  | Fibroblasts | − |
| Heart | Cardiocytes | −/+ |
| gut: all parts | Endothelial | − |
|  | Paneth cells | +++ |
|  | Smooth muscle | − |
|  | Epithelium | − |
| Kidney | Endothelial | −/+ |
|  | Tubules | −/+ |
| Skin | Endothelial | − |
|  | nerve bundle | −/+ |
|  | Epidermis | +/− |
|  | Smooth muscle | − |
| fetal liver | RBC blasts | +++ |
|  | Macrophages | − |
|  | RBCs | Some + |
| Liver | Hepatocytes | +/− |
| Pancreas | Islets | +/− |
|  | Epithelium | −/+ |
|  | Miscl |  |
| Lung | Macrophages | −/+ |
|  | Endothelial | − |
|  | Smooth muscle | − |
|  | Epithelium | − |
| Ovary | Smooth muscle | − |
|  | Epithelium | − |
| Testis | Spermatids | −/+ |
|  | Smooth muscle | −/+ |
| Tonsil | WBCs | − |
|  | Endothelial | −/+ |
| Uterus | Smooth muscle | −/+ |
| Placenta | Endothelial | − |
|  | Epithelium | +/− |
|  | RBCs | +/++ |
| prostate | Epithelium | − |
|  | Smooth muscle | −/+ |
| spleen | Macrophages | +/− |
|  | WBCs | − |
|  | RBCs | ++/+ |
|  | Endothelial | +/++ |
| thyroid | Epithelium | −/+ |

Key:
−: negative;
−/+: negative with hint of labeling,
+: week labeling;
+/++: weak to moderate labeling;
++: moderate labeling;
++/+++: moderate to strong labeling and
+++: strong labeling.

The results suggest a role for the splice variant in specific tissues.

EXAMPLE 12

Binding Assay

All the following procedures are carried out at 4° C. Cells with stable transfected human calcium channel $\alpha_2\delta$-4 subunit are washed with PBS and suspended in lysis buffer (10 mM Tris-HCl pH7.5, 2 mM EDTA and proteinase inhibitor cocktail). The cells are incubated on ice for 40 minutes followed by brief sonication. The cell debris is removed by centrifuge at 1000×g for 10 minutes, and then the supernatant is centrifuged for 1 hour at 50,000×g. The pellet is resuspended in the lysis buffer and kept in 80° C.

The binding assay is carried out in a final volume of 250 µl containing 50 µg cell membrane, 20 mM of [$^3$H] gabapentin and 10 mM Hepes buffer, pH 7.5. After incubation at room temperature for 45 min, the reaction mixture is filtered onto pre-wetted GF/C membranes and washed five times with ice cold 50 mM Tris buffer, pH 7.5. The filters are then dried and counted in a liquid scintillation counter. For screening novel $\alpha_2\delta$-4 subunit ligand, the ability of the compounds to inhibit [$^3$H] gabapentin binding to $\alpha_2\delta$-4 subunit is determined with the same assay in the presence of the compounds.

EXAMPLE 12

Formation of a Stable Complex of $\alpha_2\delta$-4 with other Calcium Channel Subunits in HEK293 Cells Since the calcium channel is a multisubunit protein complex, a functional $\alpha_2\delta$-4 subunit, like other known $\alpha_2\delta$ subunits, would be a component of the complex. Formation of a stable complex of $\alpha_2\delta$-4 with other channel subunits was tested by coimmunprecipitation. The $\alpha_2\delta$-4 subunit was first tagged with an HA epitope and co-transfected with $Ca_V1.2$ ($\alpha_{1C}$) and $\beta_3$ subunits into HEK cells. Co-immunoprecipitation was carried out with transient transfected HEK 293 cells by constructs of $\alpha_{1C}$, $\beta_3$ and $\alpha_2\delta$-4 tagged with HA epitope. Two days after the transfection, the cells (from two 150 mm plates) were harvested and washed with PBS. The cells were then resuspended in 2 ml of detergent extraction buffer: 1% (vol/vol) Nonidet P-40, 0.5% deoxycholate, 150 mM NaCl, 5 mM EDTA, 50 mM Tris-HCl (pH 8.0) and 20 µl of protease inhibitor cocktail (Sigma), followed 10 passages each through 20 and 26-gauge needles. Cell extracts were cleared by centrifugation. Co-immunoprecipitation was carried out with 500 µl the cell lysates in the presence of either 50 µl of Anti-HA (rat monoclonal antibody) Affinity Matrix (Roche Diagnostic) or 50 µl of anti-$\alpha_{1C}$ polyclonal antibody (Alamone Labs) and 50 µl of Protein A Sepharose™ CL-4B (Pharmacia). After incubated at 4° C. for overnight, the beads were precipitated by brief centrifugation, and washed 3 times with 1 ml of lysis buffer. Finally, 100 µl of 1×SDS loading buffer were added, and 20 µl were subjected to 4–20% SDS. The co-precipitated subunits were then analyzed by Western blot with indicated antibodies.

Our results show that $\alpha_2\delta$-4 is associated with $Ca_V1.2$ and $\beta_3$ after cotransfection in HEK293 cells. The expression of all three subunits in HEK293 cells was confirmed by Western blot. Protein $\alpha_2\delta$-4(HA) was detected by both anti-$\alpha_2\delta$-4 and anti-HA Abs. $\alpha_2\delta$-4(HA), was immunoprecipitated from lysates with anti-HA Ab, and the presence of $Ca_V1.2$, $\alpha_2\delta$-4 and $\beta_3$ in the precipitates were confirmed by Western blot using anti-$Ca_V1.2$, anti-$\alpha_2\delta$-4 or anti-$\beta_3$ polyclonal Abs. Under the same condition, no subunits were immunoprecipitated from the cells transfected by only vector, pcDNA3.1. A reciprocal immunoprecipitation of $Ca_V1.2$ subunit from the same lysates was performed by using anti-$Ca_V1.2$ Ab/protein-A beads, and the presence of $\alpha_2\delta$-4 (HA) was confirmed by Western blot with anti-HA Ab. The specific co-immunoprecipitation of $\alpha_2\delta$-4(HA) subunit was further confirmed by a negative control, in which only protein-A beads were added.

EXAMPLE 13

Calcium Influx Assay

HEK 293 cells were seeded in 6-well plate (1.5×10$^5$/well) the day before the transfection. The cells were transfected with 1 μg DNA of each construct as indicated using Genejammer™ transfection reagent (Stratagene, La Jolla, Calif.) following the protocol provided by the company. After 24 hours of the transfection, the transfected cells were re-plated into 96-well plate ($2\times10^3$/100 μl/well) and incubated at 37° C./5% $CO_2$ for another 24 hours.

Figure 2:
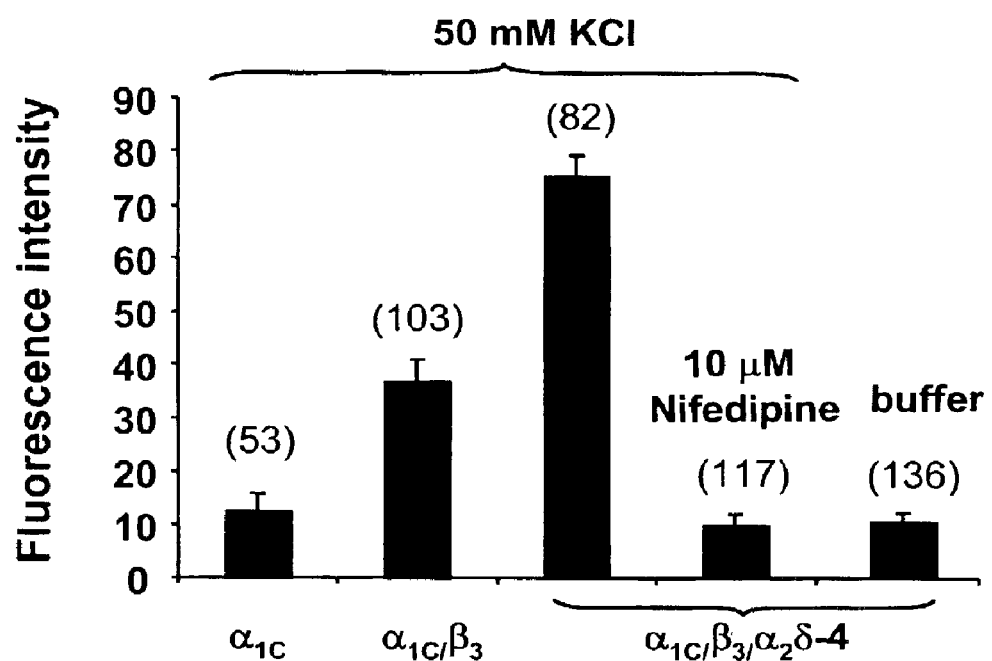
FIG. 2 illustrates the results from $Ca^{2+}$ influx assay. Cells transfected with different combination of expression constructs and loaded with $Ca^{2+}$ Plus Dye for 1 hour at 37° C. The cells were then depolarized by adding KCl to the medium (to a final concentration 50 mM) and intracellular [$Ca^{2+}$] changes were measured in individual cells by fluorescence videomicroscopy using the Attofluor Digital Imaging system. To block $Ca^{2+}$ influx, 10 µM of Nifedipine was added before the depolarization. Each bar graph represents the mean±SEM of peak fluorescence changes after depolarization. The number of assayed cells is indicated on each bar graph.

Calcium influx was measured with Attofluor Digital Imaging System. The transfected HEK 293 cells were loaded with equal volume (100 μl) of Calcium Plus Dye (*Molecular Device*, Sunnyvale, Calif.) with 2.5 mM of Probenecid for 1 hour at 37° C. The calcium channel was activated by depolarizing the cells with 50 mM KCl or with buffer only as a negative control. The calcium plus dye was excited using a RatioArc High-Speed Excitor at 488-nm wavelength. Emitted light was transmitted through a 490-nm long pass filter and collected to the Attofluor-intensified CCD camera. The fluorescence dye single wavelength images were digitized, and analyzed, using Aftofluor Ratio Vision software. Data from individual cells were collected from several experiments and exported into Microsoft Excel for further analysis. The bar graph depicted in FIG. 2 showed the means±SEM of fluorescence change after addition of 50 mM KCl. To confirm the calcium influx via the transfected $\alpha_{1C}$ L-type channel, 10 μM of Nifedipine, a specific L-type calcium channel blocker, was added before the depolarization by KCl.

As shown in FIG. 2, upon depolarization, the $Ca^{2+}$ influx in transfected cells was mediated by a Nifedipine sensitive $Ca^{2+}$ channel, presumably by over-expressed $Ca_V1.2$ ($\alpha_{1C}$) L-type $Ca^{2+}$ channel. The $Ca^{2+}$ influx in $Ca_V1.2$ transfected cells was significantly increased (~3 folds) by co-transfection of $\beta_3$ subunit. The effect was further increased to 6-fold in the presence of both $\beta_3$ and $\alpha_2\delta$-4 subunits. This result suggests that $\alpha_2\delta$-4 subunit plays a similar basic role as that of $\alpha_2\delta$-1 in formation a functional channel.

What is claimed is:

1. An isolated nucleic acid molecule selected from the group consisting of:
   (a) a polynucleotide encoding a polypeptide comprising SEQ ID NO:10;
   (b) a polynucleotide comprising SEQ ID NO:9; and
   (c) a polynucleotide comprising a sequence that is complementary to the polynucleotide of (a) or (b).

2. The nucleic acid molecule of claim 1 wherein the polynucleotide is RNA.

3. The nucleic acid molecule of claim 1 wherein the polynucleotide is DNA.

4. An expression vector comprising the nucleic acid molecule of claim 1.

5. A cultured recombinant host cell comprising the expression vector of claim 4.

6. A method for expressing an α2δ-4 calcium channel subunit protein in a recombinant host cell, comprising the steps of:
   (a) introducing an expression vector comprising a polynucleotide sequence of claim 1 into a cell; and
   (b) culturing the cells under conditions that allow expression of an α2δ-4 calcium channel subunit protein from the expression vector.

* * * * *